United States Patent
Stamer et al.

(10) Patent No.: US 7,803,558 B2
(45) Date of Patent: Sep. 28, 2010

(54) MODULATION OF AQUEOUS HUMOR OUTFLOW BY TARGETING VASCULAR-ENDOTHELIAL-CADHERIN IN SCHLEMM'S CANAL CELLS

(75) Inventors: W Daniel Stamer, Tucson, AZ (US); Ronald L Heimark, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 12/141,162

(22) Filed: Jun. 18, 2008

(65) Prior Publication Data
US 2009/0029404 A1    Jan. 29, 2009

Related U.S. Application Data

(62) Division of application No. 10/778,146, filed on Feb. 17, 2004, now abandoned.

(60) Provisional application No. 60/447,490, filed on Feb. 14, 2003.

(51) Int. Cl.
*G01N 33/53* (2006.01)
(52) U.S. Cl. ........................ 435/7.1; 435/7.21
(58) Field of Classification Search ........................ None
See application file for complete search history.

(56) References Cited

U.S. PATENT DOCUMENTS

| | | | |
|---|---|---|---|
| 5,798,380 A | 8/1998 | Kaufman et al. | |
| 6,110,912 A | 8/2000 | Kaufman et al. | |
| 6,358,920 B1 | 3/2002 | Blaschuk et al. | |
| 6,586,425 B2 | 7/2003 | Kaufman et al. | |
| 6,610,821 B1 | 8/2003 | Blaschuk et al. | |
| 2001/0053766 A1* | 12/2001 | Kumar et al. | 514/18 |
| 2002/0045585 A1 | 4/2002 | Kaufman et al. | |
| 2002/0160003 A1 | 10/2002 | Liao et al. | |

FOREIGN PATENT DOCUMENTS

| | | |
|---|---|---|
| WO | 98/25946 | 6/1998 |
| WO | 01/75109 | 10/2001 |
| WO | WO 02/87564 | * 4/2002 |

OTHER PUBLICATIONS

Erickson and Schroeder. Direct Effects of Muscarinic Agents on the Outflow Pathways in Human Eyes. Investigative Ophthalmology and Visual Science. 2000;41:1743-1748.*

Bárány EH. The mode of action of pilocarpine on outflow resistance in the eye of a primate (Cercopithecus ethiops). Invest. Ophthalmol. Vis. Sci. 1962, 1 (6): 712-727.*

Winter et al. Histamine selectively interrupts VE-cadherin adhesion independently of capacitive calcium entry. Am J Physiol Lung Cell Mol Physiol 287: L816-L823, 2004.*

Alvarado et al. Effect of beta-adrenergic agonists on paracellular width and fluid flow across outflow pathway cells. Invest Ophthalmol Vis Sci. Sep. 1998;39(10):1813-22.*

Stamer et al. Hydraulic Pressure Stimulates Adenosine 3',5'-Cyclic Monophosphate Accumulation in Endothelial Cells from Schlemm's Canal . Investigative Ophthalmology and Visual Science. 1999;40:1983-1988.*

Cochlovius, et al., Therapeutic Antibodies: After years of promise, magic bullets appear to be on the upswing. Modern Drug Discovery, 2003, pp. 33-38.

Heimark, et al. Human Schlemm's canal cells express the endothelial adherens proteins, VE-cadherin and PECAM-1. Curr Eye Res., Nov. 2002;25(5):299-308.

Liao, et al., Identification of antibody-based VE-cadherin antagonists for the application of anti-angiogenesis therapy, Proc. Nat'l Acad. Aci. USA, vol. 41, Mar. 2000, Abstract #4096.

Huang. Structural chemistry and therapeutic intervention of protein-protein interactions in immune response. HIV entry and apoptosis. Pharmacology & Therapeutics, 86: 201-215, 2000.

Corada, et al. Vascular endothelial-cadherin is an important determinant of microvascular integrity in vivo. Proc Nat'l Acad Sci USA Aug. 17, 1999;96(17):9815-20.

Gonzalez, et al. Expression Analysis of the Matrix GLA Protein and VE-Cadherin Gene Promoters in the Outflow Pathway. Invest. Ophthalmol Vis Sci. 2004;45:1389-1985.

Geiger, et al. The molecular basis for cell adhesion. Department of Molecular Cell Biology. pp. 158-159, 2000. (http://www.weizmann.ac.il/Biology/open_day_2000/images/geiger.pdf).

The Merck Manual of Diagnosis and Therapy. Glaucoma. pp. 733-738. 1999.

Mariotti, Perotti, Sessa & Rüegg. N-cadherin as a therapeutic target in cancer. Expert Opin. Investig. Drugs (2007) 16(4):451-465.

Derycke and Bracke. N-cadherin in the spotlight of cell-cell adhesion, differentiation, embryogenesis, invasion and signaling. Int. J. Dev. Biol. 48:463-476 (2004).

* cited by examiner

*Primary Examiner*—Maher M Haddad
(74) *Attorney, Agent, or Firm*—Oblon, Spivak, McClelland, Maier & Neustadt, L.L.P.

(57) ABSTRACT

The present invention provides methods of inhibiting cadherins between Schlemm's canal cells, to a patient suffering from glaucoma as well as screening for substances that inhibit cadherins between the Schlemm's canal cells.

8 Claims, 8 Drawing Sheets

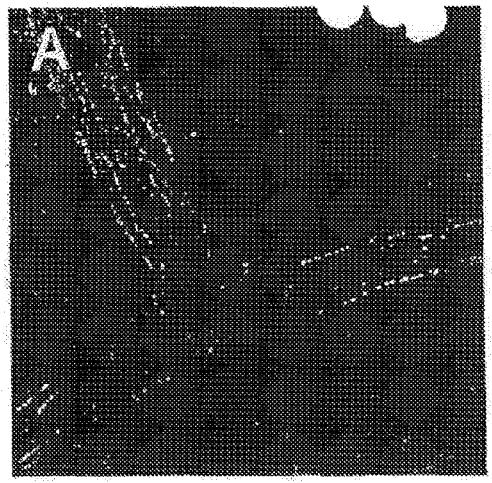
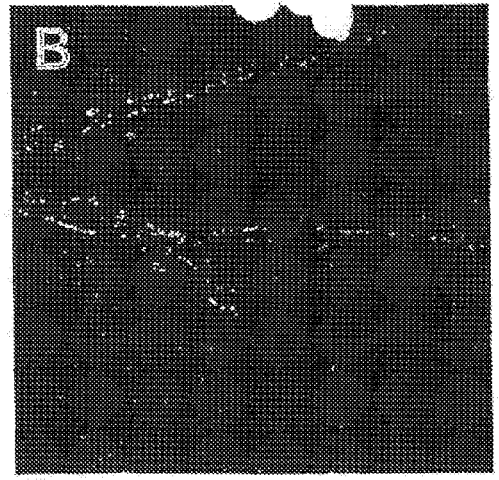
FIG. 1A
FIG. 1B
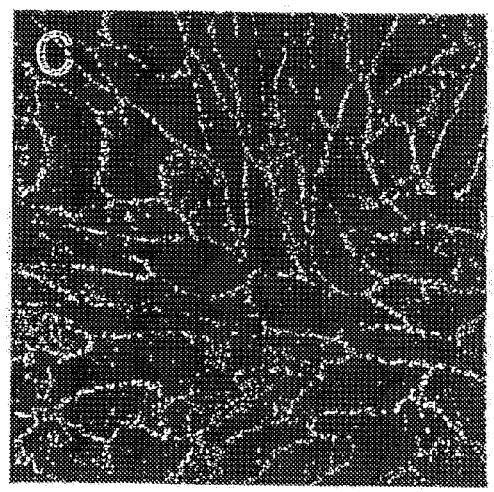
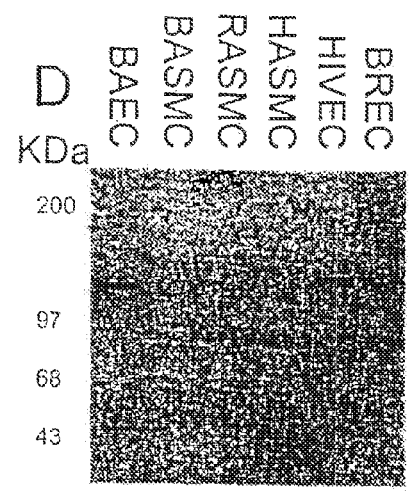
FIG. 1C
FIG. 1D

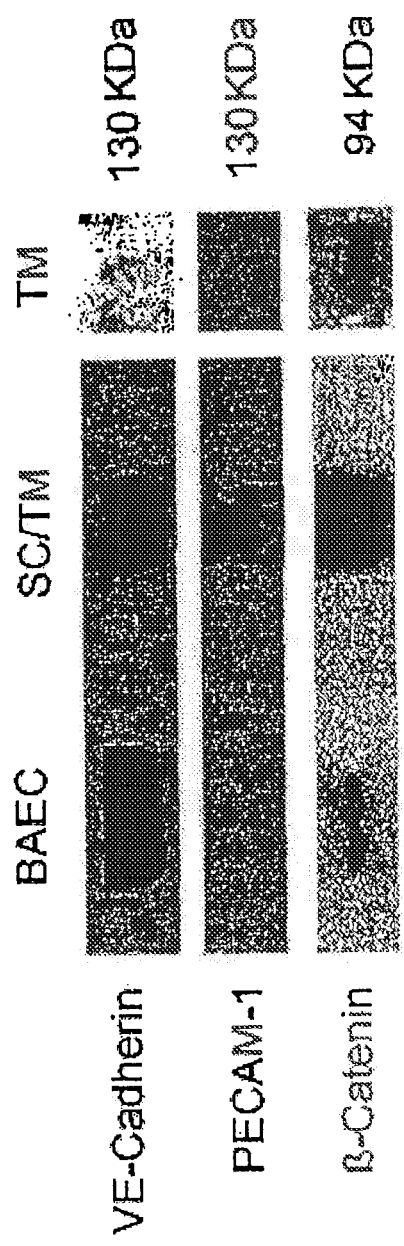
FIG. 2
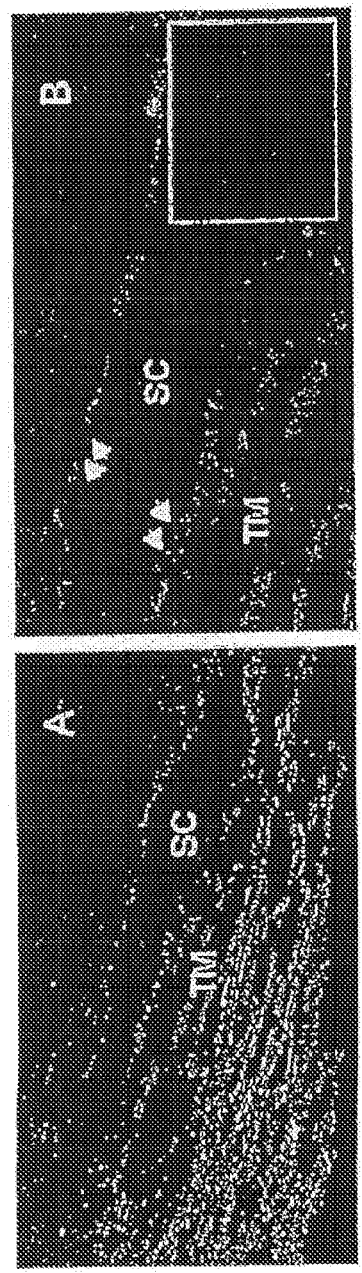
FIG. 3A
FIG. 3B
VE-cadherin

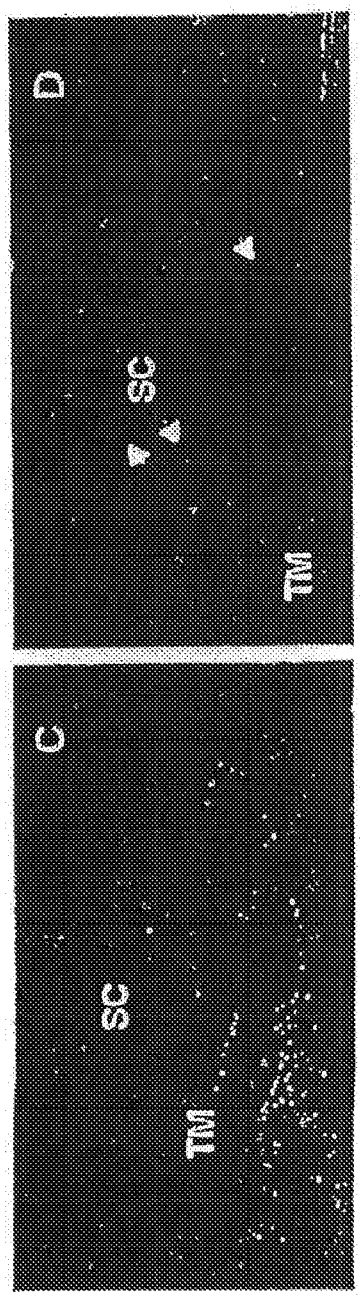
FIG. 3C
FIG. 3D
PECAM-1
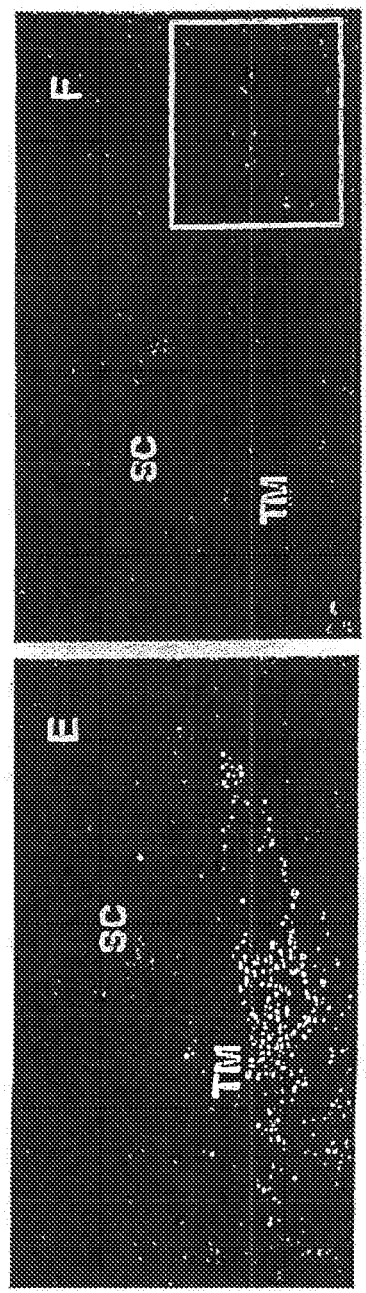
FIG. 3E
FIG. 3F
Control

MODULATION OF AQUEOUS HUMOR OUTFLOW BY TARGETING VASCULAR-ENDOTHELIAL-CADHERIN IN SCHLEMM'S CANAL CELLS

CROSS-REFERENCE TO RELATED APPLICATIONS

The present application is a divisional of U.S. patent application Ser. No. 10/778,146, filed on Feb. 17, 2004, now abandoned which claims priority to U.S. provisional patent application 60/447,490, filed on Feb. 14, 2003, the contents of which are hereby incorporated by reference in their entirety.

STATEMENT REGARDING FEDERALLY SPONSORED RESEARCH

Funding for the work described herein was provided in part by the Federal government, which has certain rights in the invention.

BACKGROUND OF THE INVENTION

1. Field of the Invention

The present invention relates to the modulation of aqueous humor outflow by targeting cadherins between Schlemm's canal cells and methods of treating glaucoma by employing cadherin inhibitors.

2. Description of the Background

Glaucoma is the second leading cause of blindness in the United States. (Quigley H. *Br J. Opthalmol.* 1996; 80:389-393.) The most common form, open-angle glaucoma, is characterized by elevated intraocular pressure (IOP) that compresses nerve axons resulting in loss of ganglion cells and subsequent loss of vision. (Quigley H et al. *Am J. Opthalmol.* 1983; 95:673-691) IOP is maintained by a balance between production and removal of aqueous humor from the eye. A reduction in removal aqueous humor elevates IOP and often leads to glaucoma. (Rohen J. *Opthalmol.* 1983; 95:673-691) The primary pathway in humans for removal of aqueous humor consists of the trabecular meshwork (TM) and the canal of Schlemm (SC). The majority of resistance to outflow of aqueous humor is generated deep in the TM (juxtacanalicular region) near or at the inner wall of SC. (Grant WM. *Arch Opthalmol.* 1963; 69:783; Bill A, Maepea O. Mechanisms and routes of aqueous humor drainage. Philadelphia: WB Saunders, 1975:206-226).

Intercellular adhesion is mediated by specific cell surface adhesion molecules. Two classes of transmembrane cell-cell adhesion molecules are present in adherens junctions of endothelium. Associated with VE-cadherin in discrete but separate domains in the adherens junction is PECAM-1 (CD31), which is a member of the immunoglobulin superfamily of adhesion molecules. (Ferrero E, et al *FEBS Letters.* 1995; 374:323-326). While calcium-independent intercellular adhesion has been shown to be through PECAM-1, VE-cadherin interactions are calcium-dependent. Cadherins mediate cell-cell adhesion through specific protein-protein interactions of cytoplasmic domains (Nose A, et al *Cell.* 1990; 61:147-155). The conserved cytoplasmic domain of cadherins is required for function and deletion of the cytoplasmic domain has been shown to inhibit cell-cell adhesion. (Kintner C *Cell.* 1992; 69:225-236). A family of intracellular proteins termed the catenins ($\alpha$-catenin, $\beta$-catenin, $\gamma$-catenin, p120ctn) is associated with the cytoplasmic domain of cadherins and links the complex to cortical actin filaments (Adams C *Curr Opinion Cell Biol.* 1998; 10: 572-577). While $\alpha$catenin is the direct linkage with actin filaments, $\beta$-catenin regulates the association of the cadherin complex with the cytoskeleton and p120ctn regulates high affinity binding of the complex between adjacent cells (Roura S et al *J. Cell Biol.* 1999; 274:36734-36740; Thoreson M et al *Cell Biol.* 2000; 148:189-202). The catenins function in the dynamic regulation of cadherin adhesive function. Tyrosine and serine/threonine phosphorylation of the cadherin/catenin complex modulate the adhesive function of the adherens junction complex by decreasing the affinity of cadherin for an adjacent cadherin or the affinity of the cadherin/catenin complex with the F-actin cytoskeleton (Roura S et al *J. Cell Biol.* 1999; 274:36734-36740; Rajasekaran A, et al *J. Cell Biol.* 1996; 132:451-463). Studies suggest that the catenins also function in the assembly of ZO-1 into tight junctions by mobilization of the ZO-1 from the cytosol to the cell surface (Rajasekaran A, et al *J Cell Biol.* 1996; 132:451-463). Therefore, regulation of the balance of multiple cell-cell adhesion molecules in response to soluble and mechanical factors is likely to play a role in control of complexity and interdependence of cell junctions between SC cells (Noria S et al *Circ Res.* 1999; 85:504-514).

In general, monoclonal antibodies against the first amino terminal repeat of VE-cadherin (that include EC 1) increase permeability of endothelial monolayers in vitro and in vivo (Corada M, et al *Blood* 2001; 97:1679-1684). Upon treatment with anti-VE-cadherin antibodies, VE-cadherin redistributes on cell surface away from intercellular junctions but does not change the localization of CD31 or tight junction proteins. Thus, VE-cadherin is a key protein involved in regulating permeability of vascular endothelial (Haselton F, Heimark R. L. *J Cell Physiol.* 1997; 171:243-251; Wong R, et al *Am. J. Physiol.* 1999; 276:H736-H748).

Currently, the primary goal in the treatment of people with glaucoma is to reduce intraocular pressure either by decreasing inflow or increasing outflow of aqueous humor. There are several currently used approaches to treat glaucoma. Current pharmacological treatments in most cases insufficiently reduce pressure in those with glaucoma. Second, no commonly used method targets the primary outflow structures of the eye; a location of pathology in most glaucomas. Third, laser trabeculoplasty, the most common surgical intervention, involves damaging trabecular meshwork tissue that results in increased remodeling and increased outflow that only lasts for a short time (usually months). Fourth, if all the above do not lower intraocular pressure, a major surgical procedure, trabeculectomy, is performed. This surgical procedure has many complications associated and is only marginally successful in most cases, lasting 1-5 years.

There remains an urgent need for new and effective therapies to treat glaucoma.

SUMMARY OF THE INVENTION

The present invention is based on the discovery of the unique expression of VE-cadherin proteins between Schlemm's canal cells in the human outflow pathway thereby providing a target to decrease intraocular pressure that in turn provides a treatment for glaucoma patients.

Accordingly, one aspect of the present invention is to a method of treating glaucoma by administering to a patient in need thereof, one or more cadherin inhibitors, or compounds that decrease cadherin homotypic binding or cadherin expression to the patient in an amount to decrease cadherin-mediated adhesion or adhesion affinity between Schlemm's canal cells thereby increasing outflow facility and decreasing intraocular pressure and treating glaucoma.

In another aspect of the present invention, methods of screening for substances that inhibit the activity of cadherins between Schlemm's canal cells is also provided.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1. Characterization of VE-cadherin by immunolocalization and immunoblotting in vascular endothelium of the retina. This is a distinct compartment in the eye from the Schlemm's cell canal. (A) Whole mount immunolocalization of VE-cadherin in a large retinal arteriole. (B) Immunolocalization of VE-cadherin in retinal capillaries. (C) Immunolocalization of VE-cadherin in retinal endothelial cells cultured on glass coverslips. (D) Immunoblotting for VE-cadherin with equivalent protein from cell lysates: lane 1, bovine aortic endothelial cells (BAEC); lane 2, bovine aortic smooth muscle cells (BASMC); lane 3, rat aortic smooth muscle cells (RASMC); lane 4, human aortic smooth muscle cells (HASMC); lane 5, human iliac vascular endothelial cells (HIVEC); lane 6, Bovine retinal endothelial cells (BREC). Data shown are representative experiments of 3 total for each condition.

FIG. 2. Immunoblot analyses of VE-cadherin and PECAM-1 in cells of human outflow pathway. Immunoblots were probed with antibodies against VE-cadherin, PECAM-1 or β-catenin. The first lane is a positive control and contains lysate prepared from BAECs. Lane 2 contains lysate prepared from outflow tissue containing SC(SC/TM) that was microdisected from human cadaveric eyes. Lane 3 contains lysate prepared from cultured human trabecular meshwork cells. Data shows one representative experiment of four total.

FIG. 3. Expression of endothelial-specific proteins by human Schlemm's Canal cells. Sequential cryosections of anterior chambers from human cadaveric eye tissue were analyzed for expression of VE-cadherin (panels A and B) and PECAM-1 (panels C and D) by immunofluorescence microscopy. Arrows indicate specific labeling. Inset of panel B shows localization of VE-cadherin labeling to cell borders. Background immunofluorescence was recorded in the absence of primary antibodies (Control, panels E and F). Tissue sections were observed at two magnifications (low: panels A, C and E and high: panels B, D and F). Internal positive controls were endothelial cells that lined collector channels (inset panel F) in same tissue sections as experimental group. Data shown is one representative experiment of seven total using seven different eye bank eyes.

DETAILED DESCRIPTION OF THE INVENTION

Figures 4A, 4B:
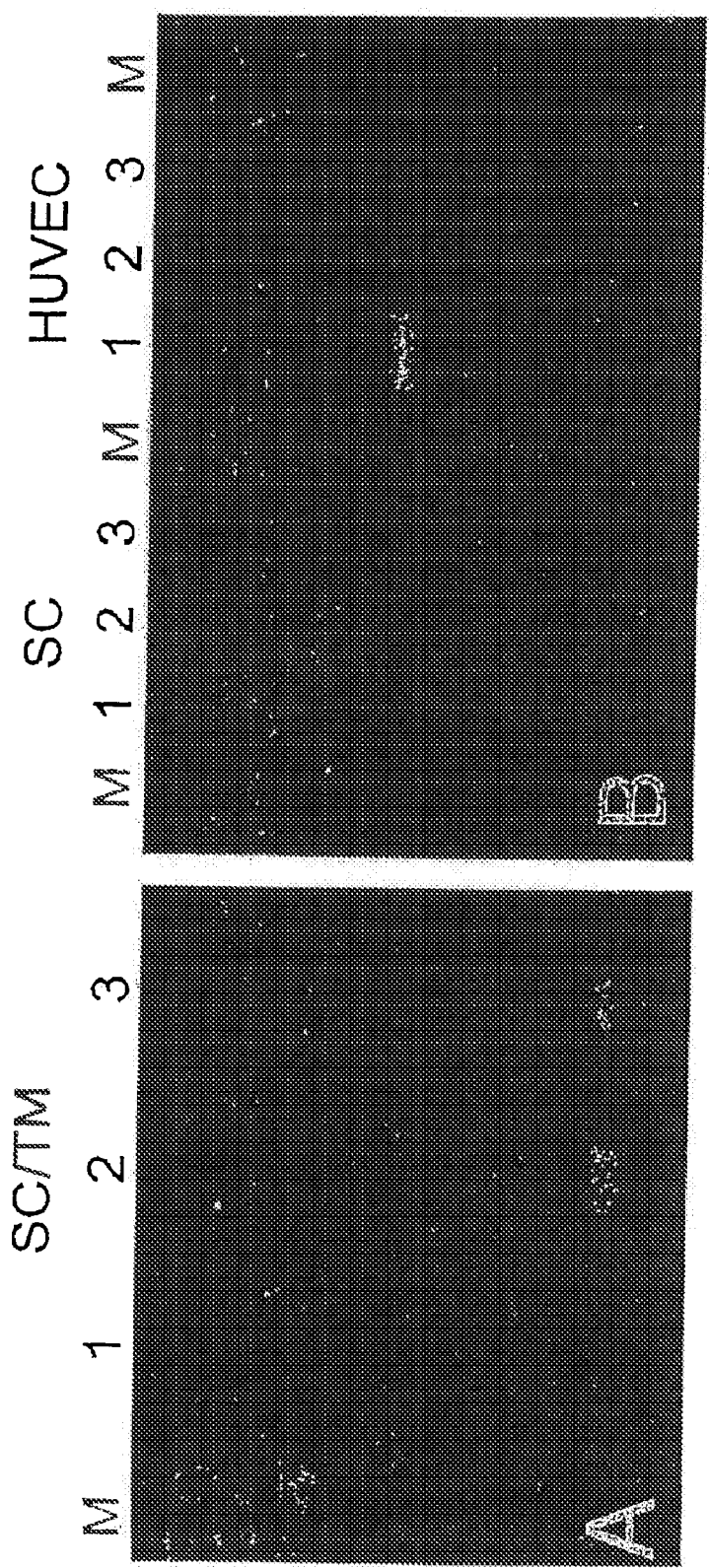
FIG. 4. By RT-PCR, cultured human SC cells express VE-cadherin mRNA. Total RNA from dissected human trabecular meshwork/SC tissue (SC/TM, lane 1, panel A) and cultured human SC cells (SC, lane 1, panel B) was analyzed for presence of VE-cadherin mRNAs by RT-PCR. To control for contamination of samples by genomic DNA, RNA was treated with RNase A before RT (lanes 2) or no template was used in PCR reaction (lanes 3). As a positive control, total RNA from HUVEC was used as template in RT-PCR (lane 1). Two VE-cadherin-specific primer sets were used. In panel A the expected product size was 308 and in panel B the expected size was 373 base pairs. All PCR products were sequenced and found to correspond identically to human VE-cadherin. Lanes M contain 100 bp marker ladders. Data shown is one representative experiment of three total for each preparation.

The present invention is based on evidence that resistance to outflow is, in part, mediated by the intercellular junctions between cells at or near the inner wall of SC. Thus, intercellular junctions can influence outflow function in at least three different ways. First, cell-cell junctional complexes maintain a contiguous inner wall of SC and limit paracellular fluid flow. (Underwood J et al *Am J Physiol.* 1999; 277:C330-C342) Second, because of a discontinuous basal lamina, SC cells may rely on cell-cell attachments from juxtacanalicular TM cells for support and/or communication. (Johnstone M. *Invest Opthalmol Vis Sci.* 1979; 18:4451) Third, cell-cell junctions join cytoskeletal elements from cell neighbors, enable the transduction of mechanical force between cells and allow the outflow tissues to function as a unit. (Wiederholt et al *Prog Retinal Eye Res.* 2000; 19:271-295).

Accordingly, the present invention provides a method of treating glaucoma by administering one or more cadherin inhibitors, or compounds that decrease cadherin homotypic binding, affinity, or cadherin expression to a mammalian patient in need thereof, in an amount such that the cadherins between the Schlemm's canal cells are inhibited in such a way to decrease intraocular pressure and/or increase intraocular outflow and in turn treat glaucoma in the mammalian patient. This invention also relates to methods for specifically targeting therapeutics toward Schlemm's canal cells by taking advantage of their unique expression of VE-cadherin amongst the lining cells of the outflow pathway. In one embodiment, the homotypic binding of cadherins is inhibited. In another embodiment, the present invention also relates to methods for down-regulating protein and mRNA expression of cadherins.

Using electron and immunofluorescence microscopy, three different morphological types of cell-cell junctions have been described in the outflow pathway: tight junctions, gap junctions and adherens junctions. (Raviola G *InvestOpthalmol Vis Sci.* 1981; 21:52-72; Grierson I *Exp Eye Res.* 1975; 20:505-522; Bhatt et al *Invest Opthalmol Vis Sci.* 1995; 36:1379-1389; Grierson I. *Graefes Arch Klin Exp Opthalmol.* 1974; 192:89-104). The lateral membrane between SC cells consists of a complex of these three junctional elements, which function together as a unit to stabilize cell-cell interaction. In contrast, the intercellular junction between SC and TM cells contains only gap and adherens junctions.

Further support for the present invention is that the proteins that form adherens junctions likely contribute to regulation of outflow resistance is as follows. First, previous studies have shown that depletion of extracellular calcium dramatically decreases outflow resistance by dissociating cell-cell interactions, thereby implicating cadherin proteins as candidates responsible for the adhesive forces in intercellular junctions of outflow cells (Bill A et al *Invest Opthalmol Vis Sci.* 1980; 19:492-504). Second, the adhesion of these proteins is highly dynamic and regulated by calcium dependent interactions of the extracellular domains and the interactions of the cytoplasmic domains with the actin cytoskeleton (Adams *Curr Opinion Cell Biol.* 1998; 10:572-577; Kintner C. *Cell.* 1992; 69:225-236). Third, increased expression of the cell adhesion protein, endothelial-leukocyte adhesion molecule (ELAM-1), was found exclusively in glaucomatous eyes compared to age-matched controls (Wang N et al *Nature Med.* 2001; 7:304-309). Lastly, extensive work in vascular endothelium has demonstrated the active participation of VE-cadherin in maintaining barrier function; (Yuan S. *Microcirculation.* 2000; 7:395-403; Corada M et al *Proc Natl Acad Sci USA.* 1999; 96:9815-9820) therefore providing a biological precedent.

Specifically targeting Schlemm's canal can be accomplished in at least two ways. First, expression of proteins that interfere with junction formation or can be targeted to Schlemm's canal cells in the conventional outflow pathway using an expression vector that contains the cadherin-5 gene promoter region (CDH5 on chromosome 16). The region contains the cis-regulatory elements necessary for VE-cadherin mRNA expression. Second, monoclonal antibodies or interfering peptides (or peptide mimetics) can be injected into the anterior chamber of eyes (or applied topically) and directed naturally to primary outflow tissues (due to aqueous humor flow pattern), in addition other inhibitory substances as described herein may also be used. Interference with cadherin adherins junction, e.g., VE-cadherinjunction, formation will result in increased permeability of Schlemm's canal, increased outflow facility and decreased intraocular pressure.

The advantages to the present invention over currently used approaches are many. As discussed above current pharmacological treatments in most cases insufficiently reduce pressure in those with glaucoma nor do the treatments target the primary outflow structures of the eye; the location of pathology. The most common surgical intervention, laser trabeculoplasty involves damaging trabecular meshwork tissue that results in increased remodeling and increased outflow that only lasts for a short time (usually months). If all the above do not lower intraocular pressure, a major surgical procedure, trabeculectomy, is performed. This surgical procedure has many complications associated and is only marginally successful in most cases lasting 1-5 years.

The region at or near Schlemm's canal is thought responsible for generating greater than 70% of resistance to aqueous humor outflow (Grant WM. Arch Opthalmol 1963; 69:783; Bill A, Maepea 0. Mechanisms and routes of aqueous humor drainage. Philadelphia: WB Saunders, 1975:206-226). The use of interventions that target cadherins, e.g., VE-cadherin, will directly affect the primary outflow pathway, will theoretically not damage trabecular meshwork tissue (no VE-cadherin protein is expressed here), is reversible and will theoretically act to flush accumulated debris in outflow pathway.

Cadherin proteins are known, for example, the sequence of N-cadherin is accessible from Genbank under the accession number X54315 and the sequence of the VE-cadherin protein is accessible from Genbank under the accession number X59796. The nucleotide sequence of N-cadherin is shown in SEQ ID NO:5 and the corresponding amino acid sequence is shown in SEQ ID NO:6. The nucleotide sequence of VE-cadherin is shown in SEQ ID NO:7 and the corresponding amino acid sequence is shown in SEQ ID NO:8. Other cadherinsequences are accessible from GenBank under the numbers NM001795, X79981, AB035304, U84722, AC012325, AC132186, NM001792, BC036470, S42303, M34064, X57548, AC015933, Z27432, AC006249, Z27420, AK129728, Z27419, AY008776, and Z27435.

Accordingly, the cadherins that are inhibited herein are preferably those described above, i.e., SEQ ID NOS:6 and/or 8 as well as the proteins that are at least 70%, preferably at least 80%, more preferably at least 90% identical to those sequences. In another embodiment, the cadherin that is to be inhibited are encoded by polynucleotide sequence with at least 70%, preferably 80%, more preferably at least 90%, 95%, and 97% identity to the cadherin sequences described above, e.g., SEQ ID NOS:5 and/or 7, these polynucleotides will hybridize under stringent conditions to the coding or non-coding polynucleotide sequence above.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995)). Amino acid and polynucleotide identity, homology and/or similarity can be determined using the ClustalW algorithm, MEGALIGN™, Lasergene, Wisconsin)

In one embodiment of the present invention inhibiting cadherin also comprises treating, ameliorating, and/or providing a prophylactic therapeutic effect for those individuals suffering from glaucoma.

By "treating" is meant the slowing, interrupting, arresting or stopping of the progression of the disease or condition and does not necessarily require the complete elimination of all disease symptoms and signs. "Preventing" is intended to include the prophylaxis of the neurological disease, wherein "prophylaxis" is understood to be any degree of inhibition of the time of onset or severity of signs or symptoms of the disease or condition, including, but not limited to, the complete prevention of the disease or condition. The substances which inhibit cadherin(s) are herein collectively termed "cadherin inhibitor(s)."

Polyclonal, monoclonal and/or fragments (e.g., Fab fragments) of antibodies that specifically bind to the cadherin proteins described herein may be used so long as they inhibit the function of the cadherins according to the disclosure herein. Obtaining polyclonal, monoclonal and/or functional fragments thereof is conventional and is described, for example, in Harlow and Lane "Using Antibodies: A Laboratory Manual" © Cold Spring Harbor Laboratory Press, Cold Spring Harbor, N.Y. (1999).

Cadherin adhesive functions depend on both the homotypic interactions of the extracellular domains on adjacent cells as well as the interaction of the cytoplasmic domain with the actin cytoskeleton. Specific peptides to the HAV sequence in the first cadherin repeat in E-cadherin and N-cadherin have been shown to interfere with adhesive functions (Blaschuk et al, *Dev Biol* 1990 139, 227-229; Williams et al, *Neuron* 1994 13, 583-594; Noe et al *J Cell Science* 1999; 112, 127-135). This sequence is not present in human VE-cadherin. Alignment of the amino acids in the extracellular domain of VE-cadherin with that of N-cadherin and E-cadherin indicates that peptides containing the sequence VIV may have similar activities. Activation of signaling pathways that increase endothelial permeability have been found to alter the cytoplasmic interactions of VE-cadherin. For example, the formation of cadherin based adherens junctions (AJs) affects cytoskeletal actin arrangement that Rho GTPases (Rho, Rac and Cdc42) regulate the state of actin polymerization. Therefore, peptides comprising the amino acid sequence of HAV and/or the amino acid sequence of VIV may also be used as cadherin inhibitors.

Additional inhibitors of cadherin proteins are described, for example, in U.S. Pat. Nos. 6,277,824, 6,326,352, 6,346,512, 6,472,367, 6,472,368, 6,551,994, 6,569,996, 6,610,821, and 6,638,911, the relevant disclosures of which are incorporated herein by reference.

The discovery of the role cadherins between Schlemm's canal cells and, in particular, in modulating intraocular pressure, for example, in glaucoma patients, is significant in that it permits the identification of additional cadherin inhibitors useful for the treatment of glaucoma. Accordingly, another object of the present invention is to provide methods of screening for a substance that inhibits the function of cadherins, e.g., VE-cadherin, between Schlemm's canal cells and further for a substance that decreases intraocular pressure in a patient in need thereof. Testing the compounds for these attributes can be performed as described in Examples 1 and 2, which follows. In this method, cultured SC cells or cells obtained from a tissue sample are contact with the substance to be screened and the detection of the ability of that substance to inhibit cadherin activity between the SC cells or the ability of that substance to increase hydraulic conductivity and/or transendothelial electrical resistance between the SC cells is indicative that the substance is capable of inhibiting the cadherins, and in turn, treating glaucoma. The substances can be tested in accepted human models of the human outflow pathway: a) human anterior chamber perfusion model and b) live animal model (monkey). Test data with a similar strategy in the vascular system are published in mice and cell culture systems (PNAS, 96:9815-9820, 1999; Blood, 97:1679-1684, 2001). Further, the substance can be tested by measuring its effect on adhesion of cultured SC cells to microtiter plates that have been precoated with fusion proteins comprising all or a portion of the extracellular domain of VE-cadherin.

The substances may be biological macromolecules, e.g., proteins, or other organic chemical molecules.

The cadherin inhibitors may be administered in a variety of dosage forms that include, but are not limited to, liquid solutions or suspensions, tablets, pills, powders, suppositories, polymeric microcapsules or microvesicles, liposomes, caged compounds, and injectable or infusible solutions. The preferred form depends upon the mode of administration.

The composition may be in the form of a liquid, slurry, or sterile solid that can be dissolved in a sterile injectable medium before use. The parenteral administration is preferably intravenously. This injection can be via a syringe or comparable means. This may contain a pharmaceutically acceptable carrier. Alternatively, the compositions, e.g. containing cadherin inhibitors, may be administered via a mucosal route, in a suitable dose, and in a liquid form.

The mammal in need thereof is understood to mean one that suffers from glaucoma and/or related ocular disease that may benefit from a decrease in intraocular pressure. Any mammal in need thereof can be treated, for example, a guinea pig, dog, cat, rat, mouse, horse, cow, sheep, monkey or chimpanzee. In a preferred embodiment, the mammal is a human.

A therapeutically effective amount of the cadherin inhibitors as described herein can be used either singularly or in combination and should be used in an amount that results in some cadherin inhibition and glaucoma therapeutic effect. Such an amount can range from about 100 ng to about 10 mg/kg body weight per inhibitor or as a combination and can be determined based on age, race, sex, and other factors based on the individual patient. When the inhibitors are administered in combination, they may be premixed prior to administration, administered simultaneously, or administered singly in series.

In another embodiment, the present invention also provides a device especially suited for slow release and constant long-term application that may be an implanted mini-pump, preferably implanted subcutaneously (for example, as described in Edith Mathiowitz; (Ed.), Encyclopedia of Controlled Drug Delivery, John Wiley & Sons vol. 2, pp. 896-920, 1999). Such pumps are known to be useful in insulin therapy. Examples of such pumps include those manufactured/distributed by Animas, Dana Diabecare, Deltec Cozm, Disetronic Switzerland, Medtronic, and Nipro Amigo as well as those described, for example, in U.S. Pat. Nos. 5,474,552; 6,558,345; 6,122,536; 5,492,534; and 6,551,276, the relevant contents of which are incorporated herein by reference.

The route of administration can include the typical routes including, for example, orally, subcutaneously, transdermally, intradermally, rectally, vaginally, intramuscularly, intravenously, intraarterially, by direct injection to the brain, and parenterally. In addition, in some circumstances, pulmonary administration may be useful, e.g., pulmonary sprays and other respirable forms. In preferred embodiments, the route for administration is topical eye drops or intraocular injection.

The above-described inhibitors can be formulated for medical purposes according to standard procedures available in the art, e.g., a pharmaceutically acceptable carrier (or excipient) can be added. A carrier or excipient can be a solid, semi-solid or liquid material which can serve as a vehicle or medium for the active ingredient. The proper form and mode of administration can be selected depending on the particular characteristics of the product selected, the disease, or condition to be treated, the stage of the disease or condition, and other relevant circumstances (*Remington's Pharmaceutical Sciences*, Mack Publishing Co. (1990)). The proportion and nature of the pharmaceutically acceptable carrier or excipient are determined by the solubility and chemical properties of the substance selected the chosen route of administration, and standard pharmaceutical practice. The pharmaceutical preparation may be adapted for oral, parenteral or topical use and may be administered to the patient in the form of tablets, capsules, suppositories, solution, suspensions, or the like. The growth factors, derivatives thereof, a nucleic acid coding sequence thereof of the present invention, while effective themselves, can be formulated and administered as pharmaceutically acceptable salts, such as acid addition salts or base addition salts, for purposes of stability, convenience of crystallization, increased solubility, and the like.

Having generally described this invention, a further understanding can be obtained by reference to certain specific examples which are provided herein for purposes of illustration only and are not intended to be limiting unless otherwise specified.

EXAMPLES

Example 1

Because the inner wall of SC constitutes the only continuous monolayer of cells in the outflow pathway, describes the cadherin subtype(s) expressed by these cells and there utility for increasing outflow to treat glaucoma.

Materials and Methods

Antibodies

For identification of VE-cadherin in intercellular junctions two monoclonal antibody preparations were used. An anti-VE-cadherin (clone 55-7H1) was purchased from Pharmingen (San Diego, Calif.) and a second murine monoclonal antibody (clone 9H7) was isolated using the following approach. Balb/C mice were immunized at two subcutaneous sites with $10^6$ human umbilical vein endothelial cells (HUVECs) in phosphate-buffered saline (PBS). Beginning four weeks after the initial immunization, mice were immunized three times at two-week intervals. The spleens were removed and fused with NS-1 myeloma cells (American Type Culture Collection, Manassas, Va.) with PEG1500 (Eastman Kodak). Production, growth, and dilution subcloning of the hybridomas were done by standard methods (Heimark R et al *J. Cell Biol.* 1990; 110:1745-1756). Hybridoma supernatants were screened by ELISA assays on rat brain endothelial cells, bovine aortic endothelial cells (BAECs), and HUVECs cultured in 96 well plates using a Molecular Devices microplate reader (Heimark R et al *J. Cell Biol.* 1990; 110:1745-1756). Wells positive on the three endothelia were screened by immunoblotting with total endothelial cell lysates on the three types of endothelium with the expected molecular weight for VE-cadherin (130 kD). Clones were further tested by immunoblotting with a bacterial fusion protein containing the first two extracellular domains of V-cadherin. Supernatants of selected clones were tested for their ability to block calcium-dependent cell-cell adhesion of HUVECs. These antibody preparations were used at a 1:1000 dilution in both immunofluorescence microscopy and western blot studies. Antibodies specific for PECAM-1 (R&D Systems, Minneapolis, Minn.) were used at a 1:500 dilution in immunofluorescence studies and 1:2000 dilution in western blot studies. Antibodies specific for β-catenin were purchased from Sigma Chemical Co. (St. Louis, Mo.) and used at a 1:5000 dilution in western blot studies.

Cell Culture

Human cadaveric eye tissue was obtained from the Donor Network of Arizona, the San Diego Lions Eye Bank and Lions Eye Bank of Central Florida within 48 hours of death for whole eyes stored in moist chambers, and 96 hours for non-transplantable corneal anterior segments stored in Optisol (Chiron Vision, Clairmont, Calif.). Human SC cells were isolated from cadaveric eye tissue using gelatin-coated cannulas as described previously. (Stamer W et al *Invest Opthalmol Vis Sci.* 1998; 39:1804-1812).

Briefly, the anterior chamber of human cadaveric eyes was cut into 8 equal and radially symmetric "wedge" shaped pieces. Using a Topcon (Paramus, N.J.) operating microscope, a gelatin-coated suture (6-0 sterile nylon monofilament, Wilson Ophthalmic, Mustang, Okla.) was gently inserted into the lumen of SC and advanced into the canal. The cannulated pieces of tissue were placed in culture (Dulbecco's Modified Eagle Medium, DMEM, containing 10% fetal bovine serum, 100 units/ml penicillin G sodium, and 100 m g/ml streptomycin sulfate (Life Technologies, Grand Island, N.Y.)) and maintained at 37° C. in humidified air containing 7% CO2 for at least 3 weeks. Sutures were removed from SC and cells seeded onto 3-cm culture plates. The cell strains used in this study were isolated from non-glaucomatous donor eye tissues from four different individuals (SC3, SC6 and SC7 and SC20) of ages 55, 45, 50 and 50 years, respectively, and all have been characterized previously.

Bovine retinal endothelial cells (BREC) were isolated from bovine retinas according to the procedure of Gitlin & D'Amore (*Microvasc Res.* 1983 July; 26(1):74-80) and cultured in Dulbecco's Modified Eagle Medium (DMEM) supplemented with 10% heat inactivated fetal bovine serum (FBS; Intergen, Purchase, N.Y.) penicillin/streptomycin plus retinal extract in a 37° C., 5% CO2 atmosphere on fibronection coated plates (Gitlin J, *Microvasc Res.* 1983; 26:74-80). After two passages they were cultured on gelatin coated dishes without retinal extract. The cells bind Dil-AcLDL and are immunolabeled by anti-von Willebrand factor. Endothelial cells were isolated from adult bovine aortas (BAEC) and grown in culture as previously described 25 in DMEM containing 10% FBS. Human umbilical vein and iliac vein endothelial cells (HIVEC) were isolated from normal veins (Gimbrone M, et al *J. Cell Biol.* 1974; 60:673-684). These cultures were propagated in Medium 199 with 15% FBS supplemented with endothelial cell growth factor (25 m g/ml, Collaborative Research, Waltham, Mass.) and heparin (90 m g/ml, Sigma). Smooth muscle cells were isolated from human rat and bovine aortas by collagenase dispersion (Geisterfer A et al *Circ Res.* 1988; 62:749-756).

Cadherin Expression Screening Studies

A PCR with cDNA generated by reverse transcription of total RNA from SC cells was performed, using degenerate primers to amplify multiple cadherin subtypes (Suzuki S et al Cell Regulation. 1991; 2:261-270). cDNA was amplified from 1 µg of DNase I treated total and the cDNA product was used in a 25 µl PCR reaction using the 5' oligonucleotide primer AATGAATTCGTNTTYGAYTAYGARGG (SEQ ID NO:1) and the 3' primer AATGAATTCRTCNGCNAGYT-TYTTRAA (SEQ ID NO:2). The reaction products were next separated by a 4% agarose gel electrophoresis (3% Nusieve GTG agarose, and 1% Seakem ME agarose, FMC BioProducts, Rockland, Me.), and a cDNA fragment of about 150 bp was extracted, digested with EcoR1, and ligated into pBluescript. Bacteria (DH5, Life Technologies, Grand Island, N.Y.) were transformed and individual colonies were selected by color and antibiotic resistance. Plasmid DNA was isolated and subsequently sequenced.

Whole Mount Immunolabeling

Using a whole mount immunolabeling technique the intercellular junctions in venous and arterial segments of the retinal vasculature were labeled with anti-VE-cadherin (monoclonal antibody 9H7). Bovine retinas were dissected, fixed in 4% para-formaldehyde for 30 minutes, then permeabilized with CSK buffer containing 0.5% triton X-100, 10 mM PIPES (pH 6.8), 50 mM NaCl, 3 mM $MgCl_2$ and 0.3 M sucrose for an hour at 4° C. The retinas were blocked and incubated with the primary antibody in blocking solution. After washing the retinas with at least 5 changes of CMF/PBS with 0.1% BSA, the biotinylated-secondary anti-body was added for two hours, and then washed overnight. FITC-conjugated strepavadin was added and incubated for 30 min and then washed extensively before mounting.

Indirect Immunofluorescence Microscopy of Frozen Sections

Indirect immunofluorescence microscopy was performed on fresh frozen human eye tissue containing outflow structures. Tissue wedges that include angle structures were dissected from human eye bank eyes and embedded in OCT compound, frozen in a dry ice/ethanol bath and sectioned (8 mm). Sections on slides were fixed in 50% methanol/50% acetone and air-dried. Fixed sections of tissue were rehydrated in PBS, blocked with 10% goat serum in PBS containing 0.1% triton X-100 and incubated overnight with monoclonal IgG (1:1000 dilution, clone 9H7) or PECAM-1. Goat serum (10%, Sigma Chemical) and triton X-100 (0.1%, Sigma Chemical) were included in incubations to inhibit non-specific binding of antibodies to tissues. Following antibody incubations, tissue sections were washed extensively (4×4 ml×15 min) in phosphate-buffered saline containing 0.1% triton X-100.

Specific binding of antibodies to receptor was detected using CY3-conjugated goat anti-mouse immunoglobulin-G (IgG) or CY3-conjugated goat anti-rabbit IgG at a 1:1000 dilution (Jackson Immunoresearch Laboratories, West Grove, Pa.). Tissue sections were incubated with secondary antibodies for 2 hours and washed extensively before viewing. Background fluorescence was indicated in tissues processed in the absence of primary antibodies. Labeled tissue sections were visualized and photographed digitally using an Olympus IX70 inverted fluorescence microscope with a Magnifire digital camera (Olympus, Melville, N.Y.).

Total RNA Isolation

Total RNA was isolated from tissue dissected from human outflow pathway (including SC) and confluent cultures of SC cells in 10 cm culture plates using Trizol reagent according to the manufacturers recommendations (Life Technologies). Following extraction, RNA was precipitated using ice-cold ethanol, resuspended in diethyl pyrocarbonate (Sigma Chemical Co.)-treated water and incubated with RNAse-free DNAse (Promega, Madison, Wis.) to digest genomic DNA. RNA was extracted from DNAse using phenol/chloroform, precipitated with ethanol and resuspended in diethyl pyrocarbonate treated water. Integrity of RNA was verified following separation by electrophoresis into a 0.8% agarose gel containing formaldehyde and visualization using ethidium bromide.

Reverse-Transcription Polymerase Chain Reaction Studies

The presence of messenger RNA encoding VE-cadherin in dissected human tissue containing SC or primary cultures of SC cells was determined by RT-PCR. Utilizing Avian Myeloblastosis Virus reverse transcriptase (Boehringer Mannheim, Indianapolis, Ind.), DNA copies of total RNA were made using a primer specific for VE-cadherin (Genbank number: NM001795) antisense RNA transcripts (5'-ATCCCAT-TGTCTGAGATGACC-3' (SEQ ID NO:3) or 5'-GAGGATG-CAGAGTAAGATGG-3' (SEQ ID NO:4)) as described previously (Starner WD et al Curr Eye Res. 1995;14:1095-1100). Amplification of RT cDNA by taq polymerase (Life Technologies) was performed as previously described 31 using 30 PCR cycles (94° C. for 30 s, 55° C. for 30 s and 72° C. for 90 sec). Specific amplification of VE -cadherin cDNAs was accomplished using a primer set that corresponds uniquely to VE -cadherin (sense: 5-GAATCCATTGTG-CAAGTCCAC-3 (SEQ ID NO: 9) or 5-ACCCCTGG-TATAACCTGACT-3 (SEQ ID NO: 10) antisense: 5-ATC-CCATTGTCTGAGATGACC-3 (SEQ ID NO: 3)) and PCR products were analyzed on 1.4% agarose gels. Based upon published sequence, the expected size of a VE-cadherin PCR product is 308 or 373 base pairs, depending upon the primer set used. Two different primer sets to unique VE-cadherin sequences were tested with all RNA preparations in initial screens before sequencing. As a positive control, VE-cadherin RNA was isolated from human umbilical vein endothelial cells and mRNA encoding VE-cadherin was copied and amplified as described above. Since DNA coding VE-cadherin contains no introns, we were rigorous with controls to minimize possibility of false positive amplification of genomic DNA. Negative controls include: the exclusion of cDNA from PCR (water control), treatment of RNA with RNAse-A prior to RT reaction and the inclusion of RNA not reversed transcribed in the PCR reaction. To verify the identity of PCR-generated DNA, all of the products were sequenced in both directions.

Western Blot Analysis

Equivalent protein from sodium dodecyl sulfate (SDS) solubilized whole cell lysates containing 5% β-mercaptoethanol were electrophoresed into 7.5% polyacrylamide gels containing 0.1% SDS. Fractionated proteins were blotted onto nitrocellulose using the Transblot system as per manufacturer instructions (Biorad, Hercules, Calif.). The blots were preincubated for 30 minutes at 22° C. in Tris-buffered saline (25 mM Tris and 150 mM NaCl) containing 5% nonfat powdered milk and 0.2% Tween-20 (TBS-T), and were then probed with appropriate antibodies for 2 hr at 22° C. The blots were washed (3×15 min) in TBS-T and were incubated for 2 hours with horseradish peroxidase-conjugated secondary antibodies (goat anti-mouse, 1:5000, Pierce). The blots were washed (3×15 min) in TBS-T and specific labeling was visualized following enhanced chemiluminescence (Pierce, Rockford, Ill.) and exposure (10 seconds) to ECL-Hyperfilm (Amersham, Arlington Heights, Ill.). Immunoblots were digitized using the UVP gel documentation system and densitometry was performed using LabWorks software (Upland, Calif.).

Results

To identify the different cadherin subtypes expressed in human SC cells, cadherin cDNAs were amplified by RT-PCR using degenerate oligonucleotide primers that correspond to well-conserved amino acid sequences of the cadherin cytoplasmic domain (Suzuki S et al *Cell Regulation*. 1991; 2:261-270). A cDNA band of approximately 150 bp was amplified from two different SC cell strains, gel purified, subcloned into an expression vector and bacteria were trans-formed. Ninety-six individual bacterial clones were selected and grown in a microtiter plate and DNA from each well was transferred to nitrocellulose. Southern blot analysis using a radiolabeled probe that specifically hybridizes to N-cadherin (cadherin-2) revealed that ~45% of total clones were of the N-cadherin type (Table 1). Since N-cadherin commonly is co-expressed with VE-cadherin, the remaining clones were screened by PCR using primers that correspond uniquely to VE-cadherin (Navarro et al *J. Cell Biol*. 1998; 140:1475-1484). Approximately one third of the clones that did not hybridize to N-cadherin, (19% of total) were VE-cadherin (Table 1).

TABLE 1

Summary of cadherin expression in SC cells

|  | SC3 | SC 7 | SC SUMMARY |
| --- | --- | --- | --- |
| N-CADHERIN | 42% (20/48) | 48% (23/48) | 45% (43/96) |
| VE-CADHERIN | 24%* | 18%* | 19%** |
| OTHER*** | 34% | 34% | 36% |

*Of the 28 clones that hybridized poorly or not at all with a full-length N-Cadherin probe (Genbank # X54315) in SC3, 12 were screened by PCR for VE-cadherin (Genbank # X59796). 5/12 amplified with VE-cadherin-specific primers, so 11.67 are predicted for all 28 giving 24% of total. Similar predictions were made for SC7 where 6/17 clones sampled were positive.
**Of the clones that hybridized poorly with N-cadherin probe 43% of SC 3 and 72% of SC 7 were screened (1:1.67 ratio); the estimated percent VE-cadherin of total clones is given by: ((0.24 × 1) + (0.18 × 1.67))/2.67}× 96] = 19%.
***Other denotes clones with low or no signal in either VE or N-cadherin screen.

In order to characterize the expression of VE-cadherin in SC cells, a monoclonal antibody against VE-cadherin was first examined in bovine retinal vessels in whole mount by indirect immunofluorescence microscopy and a variety of endothelial cell lines were analyzed using western blot. Using retinas prepared by whole mount, FIG. 1A-B shows a pattern of immunoreactivity in retinal vascular endothelium characteristic of VE-cadherin. Thus, reactivity was limited to cell-cell borders and to the vascular structures of the retina. This same pattern of reactivity was observed at borders between bovine retinal endothelial cells in culture (FIG. 1C). To verify specificity of anti-VE-cadherin IgG, whole cell lysates from bovine retinal endothelial cells, bovine aortic endothelial cells, human umbilical vascular endothelial cells, human iliac endothelial cells, rat smooth muscle cells and human smooth muscle cells were analyzed by western blot (FIG. 1D). Antibodies reacted uniquely to a single protein species at approximately 130 kd, that corresponds to the predicted molecular weight of VE-cadherin. Anti-VE-cadherin antibodies were next used in western blots that analyzed tissue preparations containing SC cells. Outflow tissues containing SC vessels were microdissected from human donor eyes and were solubilized in 2% SDS. Lane 2 of FIG. 2 (SC/TM) demonstrates the presence of a protein in SC cell lysates that specifically reacts as a single band with anti-VE-cadherin IgG. This protein co-migrates with an immunoreactive protein contained in bovine aortic endothelial cells (BAEC, positive control, lane 1) at about 130 kd. We also analyzed primary cultures of TM cells (TM, lane 3) and were unable to detect VE-cadherin protein expression by these methods. Blots were stripped of antibody complexes and incubated with antibodies specific for PECAM-1 and β-catenin. Results show that β-catenin was expressed in all samples; however, PECAM-1 was only detected in the SC preparations. To visualize the location of VE-cadherin immunoreactivity observed in outflow tissue preparations by western blot, frozen sections containing SC and TM were analyzed by indirect immunofluorescence microscopy. Using wedges of tissue prepared from anterior chambers of human eye bank eyes, we examined the expression of VE-cadherin and observed specific labeling of VE-cadherin of both inner and outer wall cells of SC (FIG. 3, panel A-B). With respect to outflow structures, the labeling was limited to endothelial cells of SC and collector channels (internal positive control, inset panel F); no labeling above background was observed in the trabecular meshwork. Labeling of SC cells was characteristic of VE-cadherin and was limited to cell borders (inset panel B). We failed to see specific labeling of cornea endothelium, cornea epithelium, ciliary muscle, scleral fibroblasts and stromal fibroblasts. A similar labeling pattern was observed using antibodies against another protein that participates in adherens junctions, platelet endothelial-cell adhesion molecule-1 (PECAM-1). Panels C-D show specific immunoreactivity of SC endothelium. The trabecular mesh-work and other surrounding structures did not bind anti-PECAM-1 IgG. Panels E-F are included to demonstrate the background fluorescence and autofluorescence of anterior chamber structures under the conditions of the present experiments. To confirm independently the findings from studies using immunofluorescence microscopy and cDNA screens, RT-PCR was used with total RNA isolated from dissected tissues containing SC (SC/TM) and primary cultures of SC cells (SC) isolated specifically from human eye bank eyes. Reverse transcription was performed using total RNA isolated from outflow tissues dissected bluntly from human anterior chambers, cultured human SC cells or human umbilical vein endothelial cells; and PCR was used to amplify resulting cDNAs. With primers specific for human VE-cadherin, a single PCR product was obtained using cDNAs prepared from either human source containing SC cells (FIG. 4, lanes 1). Depending upon the primer set used, DNA products obtained (panel A 308 bp or panel B 373 bp) were the same size as those obtained using cDNA prepared from human umbilical vein endothelial cells (HUVEC, lane 1, positive control). Such PCR products were not acquired when the RNAs were treated with RNase (lanes 2) prior to RT or when cDNA was omitted from the PCR (water control, lanes 3). PCR products were sequenced and found to correspond identically to VE-cadherin.

These data demonstrate the expression of two proteins that participate in adherens junctions at borders between SC cells. PECAM-1 (CD31) protein and VE-cadherin messenger RNA and protein were expressed in SC but not trabecular meshwork cells. The significance of this report is three fold. First, it provides unambiguous data that SC cells are vascular in origin. Second, it provides the first useful markers to distinguish TM from SC cells. Third, it implicates adherens junctions as sites for regulation of resistance to aqueous humor outflow. While SC is formed from intrascleral venous plexus and SC cells contain structures that resemble Weibel-Palade bodies, immunochemical confirmation of putative endothelial nature of SC has been ambiguous. For example, SC cells reacted weakly, in patches or not at all to antibodies against an endothelial marker protein, von Willebrand factor (Wang N et al *Nature Med.* 2001; 7:304-309; Stamer W E et al *Invest Opthalmol V is Sci.* 1998; 39:1804-1812; Hamanaka T et al *Exp Eye Res.* 1992; 55:479-488; Pandolfi M. *Archiv Opthalmol.* 1976; 94:656-658). In the present study we examined the expression of two alternative endothelial-specific proteins and demonstrated that SC cells exclusively express VE-cadherin and PECAM-1 in the conventional human outflow pathway. Our findings of PECAM-1 expression in SC extend data presented previously (Wang N et al *Nature Med.* 2001; 7:304-309). Since SC cells express two proteins that contribute to permeability of vascular endothelium, we hypothesize that adherens junctions between SC cells contribute to resistance of aqueous outflow. Approximately 90% of the transendothelial solute exchange in the vascular system occurs paracellularly, regulated in part by VE-cadherin and associated proteins (Corada M et al *Proc Natl Acad Sci USA.* 1999; 96:9815-9820; Wong R et al *Am J Physiol.* 999; 276:H736-H748; Haselton F, Heimark R *J Cell Physiol.* 1997; 171: 243-251). For example, monoclonal antibodies directed at extracellular domains of VE-cadherin inhibit junction formation and dramatically increase permeability of endothelial monolayers (Haselton F, Heimark R *J Cell Physiol.* 1997; 171: 243-251; Corada M, et al *Blood.* 2001; 97:1679-1684). Additionally, a variety of stimuli that affect the rearrangement of cytoskeletal proteins at the level of adherens junctions increase permeability of endothelial monolayers (Bazzoni G, Dejana E. *Microcirculation.* 2001; 8:143-152). For example, inactivation of Rho members of the Ras superfamily of small GTP-binding proteins disrupted the barrier function of endothelial monolayers (Bazzoni G, Dejana E. *Microcirculation.* 2001; 8:143-152). Rho family members are key players in the signal transduction mecha-nisms that regulate a diverse range of intracellular activities such as the formation of actin stress fibers, lamellipodia, filopodia, as well as a number of intracellular tyrosine and serine/threonine kinases (Fukata M, Kaibuchi K. *Nat Rev Mol Cell Biol.* 2001; 2:887-897). With respect to SC endothelia, disruption of actin cytoarchetecture or inhibition of rho GTPase results in increased outflow facility or permeability of SC monolayers (Kaufman P *Invest Opthalmol Vis Sci.* 1982; 23:646-650; Honjo M, et al *Invest Opthalmol Vis Sci.* 2001; 42:137-144; Rao P *Invest Opthalmol Vis Sci.* 2001; 42:1029-1037). Interestingly, effects of these drugs on vascular endothelia and SC endothelia are similar even though direction of flow across vascular endothelia is opposite that of flow across inner wall of SC. In addition to expressing identical adherens junction proteins at cell borders, SC cells and vascular endothelia both appear to utilize similar intercellular signaling pathways that regulate paracellular permeability. For example, SC cells express the endothelial-specific nitric oxide synthase (eNOS) (Nathanson J, McKee M. *Invest Opthalmol Vis Sci.* 1995; 36:1765-1773) and activation of this enzyme by nitric oxide-mimicking vasodilators decrease outflow resistance (Schuman J, et al *Exp Eye Res.* 1994; 58:99-105). In contrast, some signaling pathways that control vascular permeability appear to be different between vascular endothelia and SC cells. For example, venous endothelium in the eye express vascular endothelial growth factor (VEGFR)3 and endothelium of the microvasculature express VEGFR1 and VEGFR2, however there is currently no evidence that any of the receptors for VEGF are expressed in SC cells (Yamaguchi T et al *Development.* 1993; 118:489-498; Kim I, et al *Invest Opthalmol Vis Sci.* 1999; 40:2115-2121; Kubo H, et al *Proc Natl Acad Sci USA.* 2002; 99:8868-8873).

The importance of cell-cell adhesion at the level of SC in aqueous outflow facility has been suggested by several studies using a variety of compounds that are known to affect cell-cell junctions (Bill A, *Invest Opthalmol Vis Sci.* 1980; 19:492-504; Epstein D L, et al *Invest Opthalmol Vis Sci.* 1987; 28:2067-2075; Liang L-L, et al *Arch Opthalmol.* 1992; 110: 106-109; Tian B, et al *Arch Opthalmol.* 1998; 116:633-643; Peterson J, et al *Invest Opthalmol Vis Sci.* 1999:931-941). These compounds disrupted cell-cell junctions and increased aqueous outflow. Conversely, others have shown that compounds that specifically target and occlude intercellular junctions of SC decrease outflow facility (Ethier C, et al *Invest Opthalmol V is Sci.* 2001; 42:1795-1802). The regulated involvement of cell-cell junctions in aqueous outflow function was implicated using two different approaches. First, Freddo and colleagues have demonstrated that the complexity of cell-cell junctions in SC of human eyes decreased (became more labile) in response to increased intraocular pressure (Ye W, et al *Invest Opthalmol Vis Sci.* 1997; 38:2460-2468). These data for the first time implicated cell-cell junctions as a mechanism by which outflow cells respond to flow/pressure. Second, Alvarado and colleagues have shown that adrenergic agents may regulate the permeability of outflow cell monolayers (Alvarado J A, *Invest Opthalmol Vis Sci.* 1998; 39:1813-1822). For example, epinephrine increased paracellular spaces between TM and SC cells and increased cellular permeability to water in an in vitro model. Using this same approach, it has been shown that the intercellular-signaling molecule, cAMP, is affected by flow/pressure in SC cells; a response that required intact, mature cell-cell junctions (Stamer W et al *Invest Opthalmol Vis Sci.* 1999; 40:1983-1988). Taken together, the above data support that cell-cell junctions in the conventional outflow pathway of the human eye participate in the regulation of aqueous outflow resistance thereby providing a cellular pathway of potential targets for future glaucoma therapy. Pharmacological interference with the delivery to or turnover of adherens proteins at the cell surface may decrease adhesive strength between SC cells. Thus, weakening of adheren-mediated adhesive interactions between cells of the inner wall of SC can increase outflow facility.

Example 2

The purpose of the following experiments was to test the effects of $Na_2EDTA$ in vivo at the level of SC and that disruption/reformation of cell-cell junctions at level of SC represent a likely mechanism for outflow tissues to respond to transient changes in pressure.

Materials and Methods

Cell Types and Culture

SC Cells: Human cadaveric eye tissue was obtained from Donor Network of Arizona, San Diego Lions Eye Bank or North Carolina Lions Eye Bank within 48 hours of death for whole eyes stored in moist chambers, and within 96 hours for non-transplantable corneal anterior segments stored in Optisol (Chiron Vision, Clairmont, Calif.). Human SC cells were isolated from the cadaveric eye tissue using gelatin-coated cannulas, as described previously (Stamer W D, et al *Invest Opthalmol Vis Sci* 1998; 39:1804-1812) or by differential dissection (O'Brien E, *Invest. Opthalmol. Vis. Sci.* 2000; 41:3842-3849). Cells used in perfusion studies were isolated by both methods while only cells isolated by differential dissection were used in morphology experiments. Cells were grown and maintained in Dulbecco's Modified Eagle Medium (DMEM) and maintained in humidified air containing 5% $CO_2$ at 37° C., as described previously (Stamer W D, et al *Invest Opthalmol Vis Sci* 1998; 39:1804-1812). Human SC cells were seeded at 100,000 cells/cm$^2$ onto 1-cm$^2$ Snapwell Filters (Snapwell; Costar, Acton, Mass.) with 0.4-µm pore diameter in 10% FBS/DMEM. Primary cultures of eight SC cell strains were isolated from eight different cadaveric eyes without a history of glaucoma and used in the present study (SC3, SC6, SC10, SC11, SC41, SC42, SC 57 and SC68).

MDCK Cells: Madin-Darby Canine Kidney cells (MDCK), were used as a control to characterize perfusion system and for comparisons to SC monolayers. Responses of calcium-sensitive junctional complexes between MDCK cells are well documented (Nelson *J Cell Biol* 1987; 104: 1527-1537) and were the most consistent in preliminary feasibility experiments that evaluated the resolution of the perfusion system to changes in TEER and HC (compared to bovine aortic endothelial cells and calf pulmonary aortic endothelial cells). MDCK cells thus served as a positive control for comparisons with SC cells in subsequent experiments. MDCK Cells used in the present study were a gift from Dr. Ronald Lynch (University of Arizona) and were used between passages 14-16. Cells were grown in DMEM and maintained in humidified air containing 5% $CO_2$ at 37° C. for at least three weeks after reaching confluence before experimentation. Cells that were past five weeks post-confluence were not used because HC and TEER were not responsive to EDTA during the time course of the experiments.

Measurement of Transendothelial Electrical Resistance and Hydraulic Conductivity Transendothelial electrical resistance (TEER) of cell monolayers cultured on Snapwell filters was measured using a TEER measurement chamber (ENDOHM-24; World Precision Instruments) in conjunction with an epithelial voltohmmeter (EVOM; World Precision Instruments). Following three rinses with prewarmed 20 mM HEPES (Sigma, St. Louis, Mo.) buffered DMEM (serum-free, pH 7.4; HEPES-DMEM), filters were carefully transferred to the TEER measurement chamber filled with HEPES-DMEM. The background electrical resistance of medium and insert was measured (typically 12-13 Ωcm$^2$) and subtracted from measurements of filters with cells in medium. Cell monolayers were excluded from the present study if they did not exhibit mature intercellular junctional complexes, as evidenced by a minimum net TEER of 10 Ωcm$^2$ after three weeks at confluence. We chose this level of maturity because monolayers less resistive consistently failed to withstand control chamber exchanges and/or pressure gradients of 5 mmHg. Further, cell monolayers cultured on filters greater than five weeks had greater TEER, but consistently lifted off of filters during control chamber exchanges. Based upon experience with human umbilical and bovine aortic endothelial cells on similar filters, weak adherence was likely the result of cells having of a greater reliance on cell-cell associations rather than cell-matrix associations over time (Ronald Heimark, personal communication). The Snapwell filters containing the cell monolayers were then carefully placed into an Ussing-type chamber (Ussing system CHM5; World Precision Instruments, Sarasota, Fla.) filled with HEPES-DMEM and maintained at 37° C. in an air incubator for 15 minutes prior to pressure application. Filters were oriented such that the apical surface of cell monolayers faced the upstream chamber. Flow through cell monolayers was a function of the pressure gradient between the upstream and downstream compartments of the chamber. Pressure in the upstream compartment was generated by an elevated reservoir of HEPES-DMEM, with pressure recorded using a pressure transducer (AH 60-3002; Harvard Apparatus, Holliston, Mass.), while the downstream compartment was vented to atmospheric pressure. The rate of fluid flow through the chamber was calculated from the weight change per unit time of the reservoir measured using an isometric transducer (AH 60-2994; Harvard Apparatus). Pressure and weight data were recorded simultaneously at 30 times/sec onto hard drive of computer using a Data Acquisition System (MP100WSW; Biopac Systems, Inc., Santa Barbara, Calif.).

Simultaneously, TEER was recorded manually at fixed intervals using the epithelial voltohmmeter and 3M KCl-filled electrodes (DRIREF-L; WPI) positioned in measurement ports on either side of cell monolayers in the Ussing-type chamber. Cell monolayers were excluded if they did not exhibit 15 minutes of stable TEER measurement prior to exposure to pressure.

Once stable TEER was achieved, a valve between the reservoir and chamber was opened to expose the upstream chamber to pressure. TEER, flow, and pressure measurements were recorded for 20 minutes to establish baseline values. Cell monolayers were excluded if the flow rate was greater than 30 ml/min or increased dramatically between the baseline measurements, indicating a compromised cell monolayer. The medium in the upstream chamber was then exchanged with 5.0 αL HEPES-DMEM at a rate of 2.5 ml/min, and a second 10-minute baseline period was measured. An upstream chamber exchange using 5.0 ml of $Na_2EDTA$ in HEPES-DMEM was then performed, followed by a five-minute measurement period during which TEER was measured once per minute.

The upstream chamber was then rinsed with 5.0 ml HEPES-DMEM, and TEER was measured once per minute until no change was observed for three successive measurements. Hydraulic conductivity was measured continuously and TEER measurements were then taken every five minutes for the duration of the trial. Following completion of TEER and hydraulic conductivity measurements, TEER of cell monolayers was measured using a TEER measurement chamber for comparison with pre-trial TEER.

Calculation of Hydraulic Conductivity

Hydraulic conductivity was calculated in real time by Biopac data acquisition software using pressure and flow measurements. The formula used to compute hydraulic conductivity was:

$$HC = Q/(P*A)$$

Where Q is the volumetric flow rate across cell monolayers. αL/min), P is pressure (mmHg), and A is the area of a Snapwell filter (1.13 cm$^2$).

Since pressure and area are constant in the experimental paradigm, HC is dependent upon Q. Pressure applied to the monolayer is contingent upon the height of a reservoir that empties as fluid moves across cell monolayers. The initial pressure for all experiments is 6 mmHg and decreases gradually during the experiment. Q is calculated from change in weight of column of fluid over time.

SC Monolayer Morphology

Images were taken from a time-lapse video recording of SC or MDCK cells just before and after the flow of buffered 10 mM $Na_2EDTA$ reduced the extracellular calcium concentration. A 25× phase contrast objective, 4× relay magnification, real time noise reduction and contrast enhancement, Dage videocamera and a 36° microscope chamber allowed us to visualize cell responses to calcium removal in real time. A flow chamber allowed the rapid exchange of buffer medium with or without EDTA with only a brief (5-8 sec) loss of imaging. The microscope was enclosed in an insulated chamber and warmed to a constant 36° with infrared heat lamps.

The initial image was obtained with a Dage Newvicon video camera, and then processed to remove noise and to increase contrast using a Hamamatsu real time image processing system (Argus 10). The limit of resolution for this technique was ~300 nm. Images were then stored on a Panasonic time-lapse video recorder at about a 60-fold time-lapse factor.

Statistical Analyses

Paired t-tests were used to compare rate of TEER change during the baseline measurement period versus rate of TEER change during $Na_2EDTA$ treatment for SC cell monolayers and for MDCK cell monolayers. A paired t-test was also used to determine whether the percent change between the baseline measurement of HC (mean of two measurements) and the measurement of HC following $Na_2EDTA$ treatment was greater than the percent change in HC between the first and second baseline measurements. Similarly, a paired t-test was used to determine whether the percent change between the baseline measurement of HC (mean of two measurements) and the measurement of HC following washout of $Na_2EDTA$ was greater than the percent change in HC between the first and second baseline measurements.

Results

Preliminary experiments were conducted to optimize the measurement of $Na_2EDTA$ effects and pressure gradients on cell monolayers. Titration experiments revealed that a that a minimum of 25 mM $Na_2EDTA$ was required to effect both hydraulic conductivity and TEER of MDCK cell monolayers in the time course of the experiments, while only 5 mM $Na_2EDTA$ was needed for SC monolayers (n=13-15, data not shown). Lower concentrations of $Na_2EDTA$ were tested (0.5-2 mM) and found not to impact significantly HC or TEER of SC monolayers in the time course of the experiment (n=6). The optimal amount of time that was required to observe consistent changes was 5 minutes. The optimal range of pressure differentials across cell monolayers to resolve changes in hydraulic conductivity was 14-16 mmHg for MDCK and 4-6 mm Hg for SC. Higher pressures for each cell type consistently compromised integrity of cell monolayers and produced erratic data (n=5-8).

TEER Effects Hydrostatic Pressure Gradients

Figure 5:
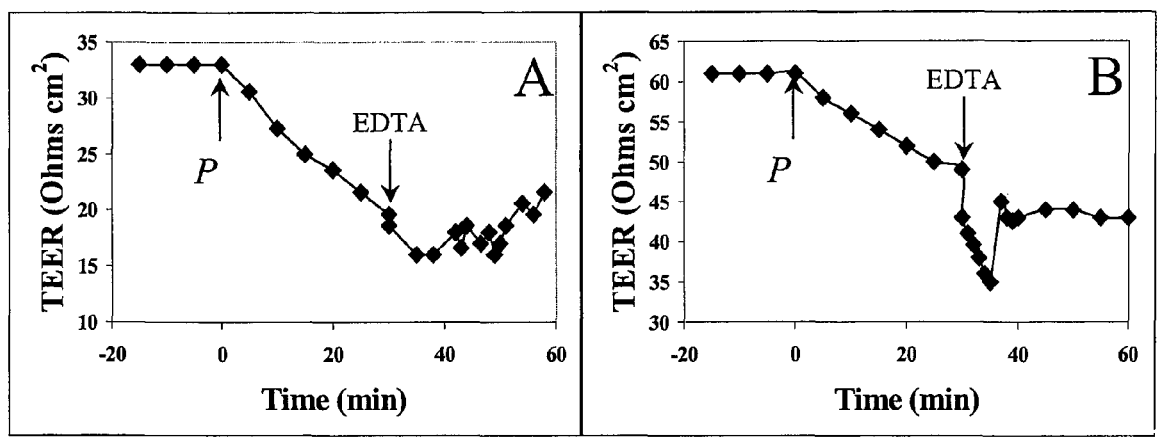
FIG. 5: Effect of hydrostatic pressure and $Na_2EDTA$ on transendothelial electrical resistance across cell monolayers. After 15 minutes of stable TEER at no pressure, either human Schlemm's canal cells (panel A) or MDCK cells (panel B) were exposed to hydrostatic pressure (P=4-6 mmHg for SC and 14-16 mm Hg for MDCK). At the 20-minute mark, chambers containing cell monolayers were exchange with normal medium (chamber exchange). At the 30-minute mark, chambers containing cell monolayers were exchanged with medium containing $Na_2EDTA$ (panel A, 5 mM and panel B, 25 mM). At the 35-minute mark, chambers containing cell monolayers were exchanged with normal medium (rinse). Shown is one experiment for each cell type of 4-5 total experiments.

The effects of hydrostatic pressure gradients (4-6 mm Hg for SC and 14-16 mm Hg for MDCK) on TEER were analyzed and compared. As shown in FIG. 5, TEER in both SC and MDCK cell monolayers was stable at atmospheric pressure. Upon exposure to a hydrostatic pressure gradient, TEER in both cell monolayers decreased. FIG. 2a shows average TEER changes for both SC and MDCK cell monolayers during a 30-minute measurement period. TEER of SC cell monolayers decreased at an average rate of 0.24 (+/−0.05 SEM) $\Omega cm^2/min$ (n=5) while TEER of MDCK cell monolayers decreased at a rate of 0.3 (+/−0.12 SEM) $\Omega/min$ (n=4). TEER changes due to exposure to hydrostatic pressure for both SC and MDCK cell monolayers were significantly different from baseline TEER measurements taken in the absence of pressure (p<0.05).

TEER Effects of $Na_2EDTA$

Figure 6:
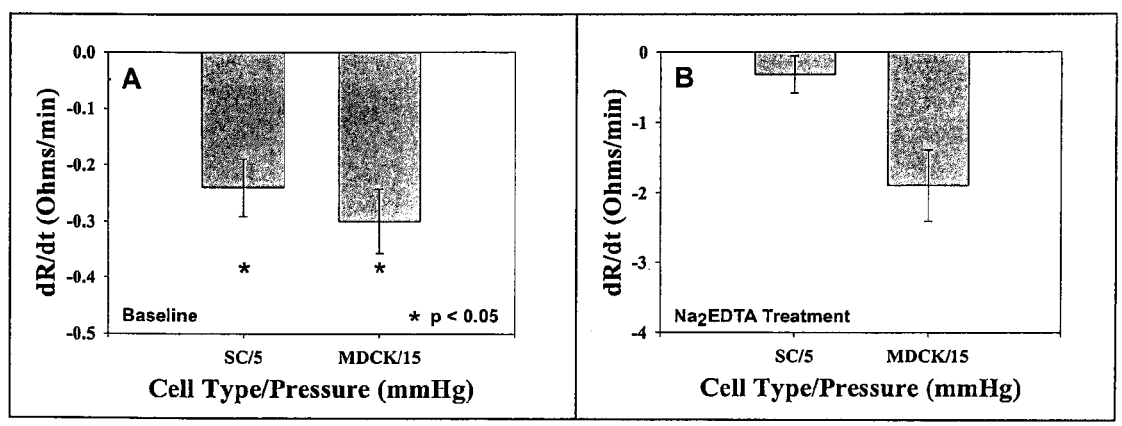
FIG. 6: Effect of hydrostatic pressure on change in transendothelial electrical resistance (TEER) across cell monolayers. Shown as histograms are the mean changes (+/−SEM) in TEER across Schlemm's Canal (SC) and MDCK cell monolayers during exposure to hydrostatic pressure either in the absence (panel A; 15 min. baseline) or presence (panel B) of $Na_2EDTA$ (5 mM for SC and 25 mM for MDCK for 5 min; measurement period=5 min. following exposure). Data represent combined data from 4-5 experiments for each cell type.

Exchange of chamber with normal medium did not affect rate of TEER change. However, after $Na_2EDTA$ treatment, TEER decreased at a new average rate of 1.9 (+/−0.12 SEM) $\Omega cm^2/min$ (n=4) in MDCK cell monolayers and 0.34 (+/− 0.26 SEM) $\Omega cm^2/min$ (n=5) in SC cell monolayers (FIGS. 5 and 6b). FIG. 5 shows effect of $Na_2EDTA$ relative to other treatments and 2b shows histogram of net average TEER changes for both SC and MDCK cell monolayers after Na2EDTA treatment. Paired t-tests showed no significant change in TEER decrease for SC cell monolayers relative to the 30-minute baseline measurement period in the presence of pressure. In contrast, MDCK cell monolayers showed a change in TEER that approached significance (p=0.06). Following rinse with normal medium, average rate of change of TEER for both SC and MDCK cell monolayers returned to levels not significantly different from pre-$Na_2EDTA$ rates for the duration of the testing period.

Effects of $Na_2EDTA$ on Hydraulic Conductivity

Figure 7:
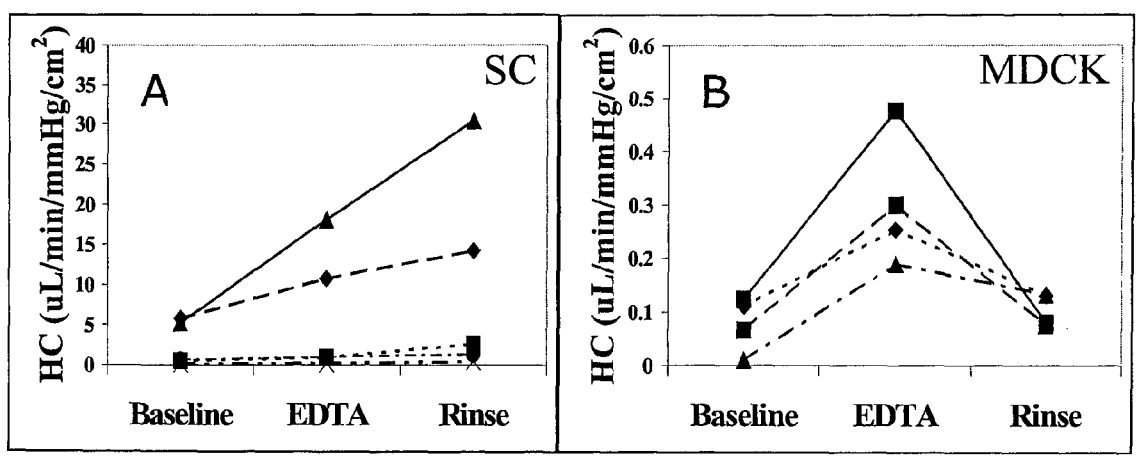
FIG. 7: Effect of $Na_2EDTA$ on hydraulic conductivity (HC) of cell monolayers. HC was calculated from continuous recording of pressure and flow across cell monolayers. After 30 minutes of stable HC across cell monolayers both before and after a chamber exchange with normal medium, SC (panel A) or MDCK (panel B) cells were subjected to medium containing $Na_2EDTA$ (5 mM for SC and 25 mM for MDCK). After 5 minutes of exposure, cells were rinsed with normal medium and HC was evaluated for 15 minutes. Monitoring of HC continued uninterrupted. Each line represents one independent experiment.

FIG. 7 shows values from individual experiments comparing hydraulic conductivity before (baseline), during (EDTA), and after (rinse) treatment with $Na_2EDTA$. SC cell monolayers were exposed to 5 mM $Na_2EDTA$ (driven by 4-6 mm Hg gradient), while MDCK cell monolayers were exposed to 25 mM $Na_2EDTA$ (driven by 14-16 mm Hg gradient) for 5 minutes.

During the 30-minute baseline measurement period, MDCK cell monolayers exhibited an average stable hydraulic conductivity of 0.038 $\alpha l/min/mmHg/cm\ 2$, compared to 2.44 $\mu l/mmHg/cm\ 2$ in SC cell monolayers. This level is consistent with permeability measurements from SC monolayers in vitro by others and about 10-fold greater than calculated in vivo (Underwood J, et al *Am J Physiol* 1999; 277:C330-C342; Alvarado J A, et al *Invest Opthalmol Vis Sci* 1998; 39:1813-1822; Johnson M, Erickson K. Mechanisms and routes of aqueous humor drainage. In: Albert D, Jakobiec F, eds. Principles and practice of opthalmology. Philadelphia: WB Saunders Co., 2000:2577-2595). As expected, baseline HC measurements were dependent upon initial TEER measurement for monolayer (table 1). Following a 5-minute $Na_2EDTA$ treatment, hydraulic conductivity of the five SC cell monolayers from four different cell strains tested increased 68%, 94%, 116%, 119%, and 230% relative to baseline. Hydraulic conductivity of the four MDCK cell monolayers increased 128%, 285%, 1664%, and 346% relative to baseline. Following chamber exchange with normal medium, hydraulic conductivity of SC cell monolayers continued to increase (123%, 156%, 406%, 505%, and 454%) relative to baseline, while MDCK cell monolayers exhibited a decrease in hydraulic conductivity to 17%, −35%, 1137%, and 12% relative to baseline during the 15 minute baseline period (table 1). In two additional experiments with SC monolayers, HC was examined two hours after $Na_2EDTA$ challenge in the presence of a pressure gradient and found to return to near baseline levels (58% and −39% relative to baseline).

Percent change in HC relative to baseline following $Na_2EDTA$ treatment was significantly greater than percent change of HC between the two baseline measurements in cells (p<0.05) and in MDCK cells (p<0.05). Percent change in HC relative to baseline following post-$Na_2EDTA$ rinse with normal medium was significantly greater than percent change between the two baseline measurements in SC cells (p<0.05) but not in MDCK cells.

TABLE 1

Hydraulic conductivity measurements of cell monolayers

| Cell Line | Net TEER | Baseline HC | Post-EDTA HC | Post-Rinse HC |
| --- | --- | --- | --- | --- |
| SC 10 | 10 | 5.79 | 10.79 | 14.22 |
| SC 10 | 15 | 0.47 | 0.95 | 2.63 |
| SC 11 | 10 | 5.25 | 18.14 | 30.44 |
| SC 41 | 14 | 0.008 | 0.18 | 0.42 |

TABLE 1-continued

Hydraulic conductivity measurements of cell monolayers

| Cell Line | Net TEER | Baseline HC | Post-EDTA HC | Post-Rinse HC |
|---|---|---|---|---|
| SC 43 | 12 | 0.61 | 1.02 | 1.36 |
| MDCK | 76 | 0.053 | 0.12 | 0.062 |
| MDCK | 78 | 0.058 | 0.22 | 0.038 |
| MDCK | 64 | 0.0062 | 0.11 | 0.077 |
| MDCK | 53 | 0.034 | 0.15 | 0.038 |

Transendothelial electrical resistance (TEER; $\Omega$ cm$^2$) measurements of cell monolayers were made using EndOhm chamber immediately prior to exposure to pressure gradient. Units for baseline, EDTA and Rinse hydraulic conductivity (HC) measurements are $\alpha$l/min/mmHg/cm$^2$.

Morphological Effects of Na$_2$EDTA

Figures 8A, 8B, 8C:
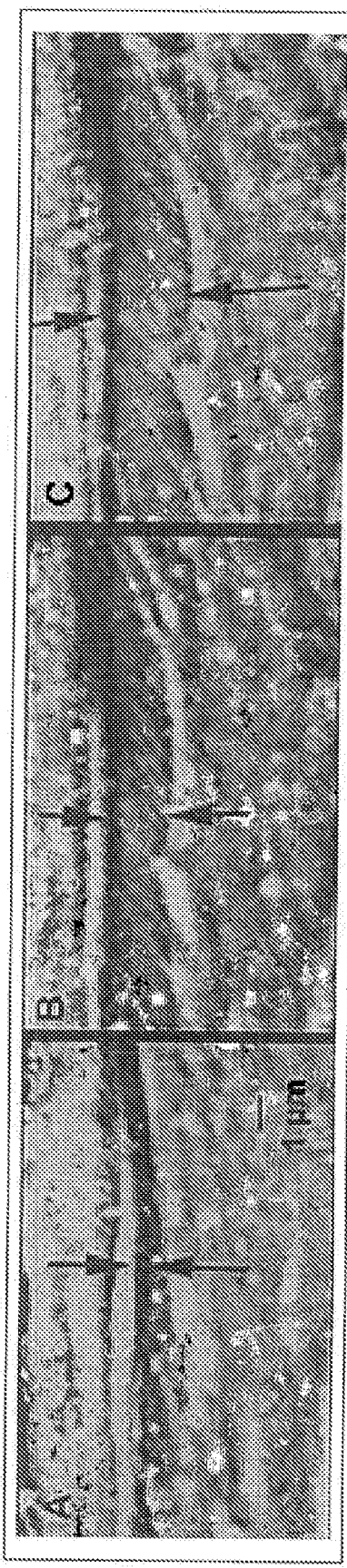
FIG. 8: Effect of $Na_2EDTA$ on cell-cell associations of Schlemm's canal monolayers. Shown in panel A is a phase-contrast image of cultured SC cell monolayers obtained by video capture before treatment with $Na_2EDTA$. Cells were exposed to 10 mM $Na_2EDTA$ for 5 minutes and rinsed with normal medium and were visualized continuously. Shown in panels B and C is the same field as in panel A, sixty and ninety seconds after treatment, respectively. The tips of arrows indicate cell margins. Retraction fibers are seen between the arrow tips in panels B and C. Shown is one representative experiment of 10 total. Images in all panels were videocaptured at the same magnification.

In parallel experiments, effects of Na$_2$EDTA on cell margins were visualized en face using phase-contrast videomicroscopy on glass coverslips. FIG. 8 shows still images captured from video sequences of live SC cell monolayers before and after Na$_2$EDTA treatment. Panel A shows the edge of 2 adjacent SC cells before exposure to Na$_2$EDTA. The tips of the arrows show the margins of the cells. The cell margins appeared to be touching to the left of arrows, and were slightly separated (<0.5 $\alpha$m) at the arrows. Separations like this were uncommon, however these areas were chosen to image because it enabled locating and tracking of cell borders during the experiment. Panels B and C show the same field of view 60 and 90 seconds after the addition of Na$_2$EDTA. The cell margins retracted about 2 µm from each other in B, and about 3 µm in C. Fine "retraction fibers" are evident in the developing space between cell margins. MDCK cell monolayers were also evaluated before and after Na$_2$EDTA treatment. MDCK cell borders retracted from a belt-like arrangement of fibers near, but off the basal surface of the cells by 60 seconds (data not shown).

Consistent with perfusion studies, cell margins that retracted as a result of exposure to Na$_2$EDTA did not immediately come back together upon removal of Na$_2$EDTA. In fact, when exposed to 10 mM Na$_2$EDTA for 5 minutes, about 30 minutes were required for the margins of the cells return to their original position after replacement of normal medium (data not shown). By time lapse, the cells appeared to follow the retraction fibers left behind during retraction (data not shown).

Discussion

These data show that permeability of cultured human SC cells respond to physiologically relevant hydrostatic pressure gradients and to the calcium chelator, Na$_2$EDTA in a manner similar to that previously observed in situ (Ye W, et al *Invest Opthalmol Vis Sci* 1997; 38:2460-2468) and in vivo, respectively (Warner D, Chu E. *Can. J. Opthalmol.* 1967; 2:226. Bill A, et al *Invest Opthalmol Vis Sci* 1980; 19:492-504). In cultured SC cell monolayers, transendothelial electrical resistance significantly decreased in response to hydrostatic pressure, and hydraulic conductivity significantly increased in response to Na$_2$EDTA. These data show that calcium-sensitive intercellular junctions of Schlemm's Canal contribute in part to the generation of resistance for aqueous humor outflow and may serve to relieve transient increases in intraocular pressure. Previous research has shown that complexity of intercellular junctions between inner wall cells of Schlemm's Canal (as indicated by fewer tight junctional strands) decreases in response to elevated pressure (Ye W, et al *Invest Opthalmol Vis Sci* 1997; 38:2460-2468). Effect of pressure gradients of 0 (atmospheric), 15 and 45 mmHg were assessed. In the present study, a hydraulic pressure gradient of 5 mm Hg was evaluated and found to significantly decrease transendothelial electrical resistance (TEER) measurements across SC cell monolayers. Since TEER is an indicator of junctional complexity between cells, these functional in vitro results are consistent with those found morphologically in situ. Such rapid changes in junctional complexity may occur in combination with increased giant vacuole formation serve to accommodate transient changes in intraocular pressure that occur routinely due to eye rubbing or ocular pulsations (Johnstone M, et al *Am J Opthalmol* 1973; 75:365-383; Grierson I, Lee W. *Exp. Eye Res.* 1974; 19:21-33). While pressure-dependent changes in giant vacuoles are well documented, data indicate that pore density of inner wall cells is not pressure-dependent (Ethier C. *Exp. Eye. Res.* 2002; 74:161-172.). This suggests that intercellular pores contribute to the long-term permeability of the inner wall while complexity of intercellular junctions and/or formation of vacuoles may contribute to short-term adaptations.

Chelation of calcium has been shown to increase aqueous humor outflow facility in vivo in two different animal models (Warner D, Chu E. *Can. J. Opthalmol.* 1967; 2:226; Bill A, et al *Invest Opthalmol Vis Sci* 1980; 19:492-504; Hamanaka T, Bill A. *Exp Eye Res* 1987; 44:171-190). The concentration of Na$_2$EDTA used with SC monolayers in the present study (0.5-10 mM) was consistent with that used in these studies (0.5-6 mM) and with the theoretical concentration needed to buffer calcium in perfusion medium (2.0 mM) plus provide a sufficient gradient to pull calcium out from intercellular junctions. The present study tested whether the effects that have been observed in vivo are present at the level of SC. The results showed that chelation of calcium by Na$_2$EDTA significantly increased hydraulic conductivity across SC cell monolayers, presumably by ligating intercellular junctions. In addition, morphological findings showed a noticeable separation of cell-cell associations following Na$_2$EDTA treatment, consistent with a decrease in complexity of cell-cell junctions. Given the hydraulic conductivity and morphological findings, a corresponding decrease in TEER following Na$_2$EDTA treatment was expected, but not measured. Failure to detect a consistent and significant change in TEER after Na$_2$EDTA treatment in SC cell monolayers may have been the result of the initial pressure-driven decrease in junctional complexity, which reduced TEER to a level (basement effect) where further TEER decreases cannot be resolved.

Increases in aqueous humor outflow due to calcium chelating agents have been shown to be reversible in vivo (Warner D, Chu E. *Can. J. Opthalmol.* 1967; 2:226; Bill A, et al *Invest Opthalmol Vis Sci* 1980; 19:492-504). In perfusion experiments, MDCK cell monolayers exhibited a partial recovery of TEER and hydraulic conductivity shortly after washout of Na$_2$EDTA. In contrast, hydraulic conductivity of SC cell monolayers took longer to approach baseline levels following washout of Na$_2$EDTA. To examine this further, we followed SC monolayers after washout of Na$_2$EDTA for longer periods of time by Video microscopy and noticed that about 30 minutes were required for cell-cell contacts to begin to return visually and 2 hours functionally via TEER measurements. The differences in recovery between MDCK (seconds) to SC (minutes to hours) are likely related to respective differences between MDCK and SC in initial junctional complexity (60 versus 28 $\Omega$cm$^2$), hydraulic conductivity (2.44 versus 0.038 $\alpha$l/min/mmHg/cm$^2$) and effects of cell culture on the ability to form mature intercellular junctions. The differences observed between these two cell types likely reflect differing roles in vivo.

In conclusion, these data using cultured SC monolayers a) are similar to previous data using intact outflow pathways and b) are consistent with the idea that calcium-sensitive intercellular junctions between Schlemm's Canal cells are likely sites of action of hydrostatic pressure gradients, $Na_2EDTA$ and other calcium chelators. The recent documentation of the unique expression of vascular endothelial cadherin in human Schlemm's canal cells but not trabecular meshwork cells in the human outflow pathway may explain these results (Heimark et al *Curr Eye Res* 2002; 25:299-308). Vascular endothelial cadherin is an endothelial-specific, calcium-sensitive intercellular junction protein that in part mediates permeability of vascular endothelium (Corada M, et al *Proc. Natl. Acad. Sci. USA* 1999; 96:9815-9820) and now represents a future therapeutic target for regulation of aqueous humor outflow in people with glaucoma. The demonstration that the experimental model described herein can detect small changes in hydraulic conductivity and transendothelial electrical resistance supports the usefulness of this model in examining efficacy of drugs that can interact with vascular endothelial cadherin or other potential targets in SC cell monolayers.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for screening for a substance that inhibits VE-cadherin protein adhesion to between Schlemm's canal cells, the method comprising
culturing Schlemm's canal cells on a plate comprising all of the extracellular domain of VE-cadherin in the presence of the substance; and measuring the adhesion of the Schlemm's canal cells to the VE-cadherin on the plate, wherein a reduction in adhesion compared to adhesion in the absence of the substance is indicative that the substance inhibits adhesion between VE-cadherin and Schlemm's canal cells.

2. The method of claim 1, wherein the Schlemm's canal cells are cultured cells.

3. The method of claim 1, wherein the Schlemm's canal cells are cells obtained from a live tissue sample.

4. The method of claim 1, wherein the Schlemm's canal cells are obtained from a post mortem eye.

5. The method of claim 1, wherein the Schlemm's canal cells are human Schlemm's canal cells.

6. The method of claim 1, wherein the VE-cadherin extracellular domain is human VE-cadherin.

7. The method of claim 5, wherein the VE-cadherin extracellular domain is human VE-cadherin.

8. The method of claim 1, wherein the substance is an antibody, antibody Fab fragment, a peptide, peptide mimetic or other organic chemical molecule.

* * * * *

SEQUENCE LISTING

```
<160> NUMBER OF SEQ ID NOS: 10

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)
<223> OTHER INFORMATION: a, c, t, g, unknown or other

<400> SEQUENCE: 1
aatgaattcg tnttygayta ygargg                                          26

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)
<223> OTHER INFORMATION: a, c, t, g, unknown or other
<220> FEATURE:
<221> NAME/KEY: modified_base
<222> LOCATION: (16)
<223> OTHER INFORMATION: a, c, t, g, unknown or other

<400> SEQUENCE: 2
aatgaattcr tcngcnagyt tyttraa                                         27

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcccattgt ctgagatgac c                                               21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                        primer

<400> SEQUENCE: 4
gaggatgcag agtaagatgg                                                  20

<210> SEQ ID NO 5
<211> LENGTH: 2853
<212> TYPE: DNA
<213> ORGANISM: Homo sapiens

<400> SEQUENCE: 5
accctggccg ctgttggtgc tgccgctgcc tcctcctcct ccgccgccgc cgccgccgcc        60
gccgcctcct ccggctcttc gctcggcccc tctccgcctc catgtgccgg atagcgggag       120
cgctgcggac cctgctgccg ctgctgctgg ccctgcttca ggcgtctgta gaggcttctg       180
gtgaaatcgc attatgcaag actggatttc ctgaagatgt ttacagtgca gtcttatcga       240
aggatgtgca tgaaggacag cctcttctca atgtgaagtt tagcaactgc aatggaaaaa       300
gaaaagtaca atatgagagc agtgagcctg cagattttaa ggtggatgaa gatggcatgg       360
tgtatgccgt gagaagcttt ccactctctt ctgagcatgc caagttcctg atatatgccc       420
aagacaaaga gacccaggaa agtggcaagt ggcagtaaaa attgagcctg aagccaacct       480
taactgagga gtcagtgaag gagtcagcag aagttaagaa aatagtgttc caagacaat        540 tcagtaagca cagtggccac ctacaaaggc agaagagaga ctgggtcatc cctccaatca       600
acttgccaga aaactccagg ggaccttttc ctcaagagct tgtcaggatc aggtctgata       660
gagataaaaa cctttcactg cggtacactg taactgggcc aggagctgac cagcctccaa       720
ctggtatctt cattatcaac cccatctcgg gtcagctgtc ggtgacaaag cccctggatc       780
gcgagcagat agcccggttt catttgaggg cacatgcagt agatattaat ggaaatcaag       840
tggagaaccc cattgacatt gtcatcaatg ttattgacat gaatgacaac agacctgagt       900
tcttacacca ggttttggaat gggacagttc ctgagggatc aaagcctgga acatatgtga       960
tgaccgtaac agcaattgat gctgacgatc ccaatgccct caatgggatg ttgaggtaca      1020
gaatcgtgtc tcaggctcca agcacccctt cacccaacat gtttacaatc aacaatgaga      1080
ctggtgacat catcacagtg gcagctggac ttgatcgaga aaaagtgcaa cagtatacgt      1140
taataattca agctacagac atggaaggaa tccccacata tggcctttca aacacagcca      1200
cggccgtcat cacagtgaca gatgtcaatg acaatcctcc agagtttact gccatgacgt      1260
tttatggtga agttcctgag aacagggtag acatcatagt agctaatcta actgtgaccg      1320
ataaggatca ccccataca ccagcctgga acgcagtgta cagaatcagt ggcggagatc       1380
ctactggacg gttcgccatc cagaccgacc caaacagcaa cgacgggtta gtcaccgtgg      1440
tcaaaccaat cgactttgaa acaaatagga tgtttgtcct tactgttgct gcagaaaatc      1500
aagtgccatt agccaaggga attcagcacc cgcctcagtc aactgcaacc gtgtctgtta      1560
cagttattga cgtaaatgaa aaccttattt tgcccccaa tcctaagatc attcgccaag       1620
aagaagggct tcatgccggt accatgttga caacattcac tgctcaggac ccagatcgat      1680
atatgcagca aaatattaga tacactaaat tatctgatcc tgccaattgg ctaaaaatag      1740
atcctgtgaa tggacaaata actacaattg ctgttttgga ccgagaatca ccaatgtgaa      1800 aaacaatat atataatgct actttccttg cttctgacaa tggaattcct cctatgagtg       1860
gaacaggaac gctgcagatc tatttacttg atattaatga caatgcccct caagtgttac      1920
ctcaagaggc agagacttgc gaaactccag accccaattc aattaatatt acagcacttg      1980
```

```
attatgacat tgatccaaat gctggaccat ttgcttttga tcttcctttα tctccagtga    2040 ctattaagag aaattggacc atcactcggc ttaatggtga ttttgctcag cttaatttaa    2100
agataaaatt tcttgaagct ggtatctatg aagttcccat cataatcaca gattcgggta    2160
atcctcccaa atcaaatatt tccatcctgc gcgtgaaggt ttgccagtgt gactccaacg    2220
gggactgcac agatgtggac aggattgtgg gtgcggggct tggcaccggt gccatcattg    2280
ccatcctgct ctgcatcatc atcctgctta tccttgtgct gatgtttgtg gtatggatga    2340
aacgccggga taagaacgc caggccaaac aacttttaat tgatccagaa gatgatgtaa    2400
gagataatat tttaaaatat gatgaagaag gtggaggaga agaagaccag gactatgact    2460
tgagccagct gcagcagcct gacactgtgg agcctgatgc catcaagcct gtgggaatcc    2520
gacgaatgga tgaaagaccc atccacgctg agccccagta tccggtccga tctgcagccc    2580
cacaccctgg agacattggg gacttcatta atgagggcct taaagcggct gacaatgacc    2640
ccacagctcc accatatgac tccctgttag tgtttgacta tgaaggcagt ggctccactg    2700
ctgggtcctt gagctccctt aattcctcaa gtagtggtgg tgagcaggac tatgattacc    2760
tgaacgactg ggggccacgg ttcaagaaac ttgctgacat gtatggtgga ggtgatgact    2820
gaacttcagg gtgaacttgg tttttggaca agt                                2853
```

<210> SEQ ID NO 6
<211> LENGTH: 906
<212> TYPE: PRT
<213> ORGANISM: Homo sapiens

<400> SEQUENCE: 6

```
Met Cys Arg Ile Ala Gly Ala Leu Arg Thr Leu Leu Pro Leu Leu Leu
1               5                   10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
        35                  40                  45

Val His Glu Gly Gln Pro Leu Leu Asn Val Lys Phe Ser Asn Cys Asn
    50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser
                85                  90                  95

Ser Glu His Ala Lys Phe Leu Ile Tyr Ala Gln Asp Lys Glu Thr Gln
            100                 105                 110

Glu Lys Trp Gln Val Ala Val Lys Leu Ser Leu Lys Pro Thr Leu Thr
        115                 120                 125

Glu Glu Ser Val Lys Glu Ser Ala Glu Val Glu Ile Val Phe Pro Arg
    130                 135                 140

Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
            180                 185                 190

Leu Arg Tyr Thr Val Thr Gly Pro Gly Ala Asp Gln Pro Pro Thr Gly
        195                 200                 205

Ile Phe Ile Ile Asn Pro Ile Ser Gly Gln Leu Ser Val Thr Lys Pro
```

-continued

```
            210                 215                 220
Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
                260                 265                 270

Asn Gly Thr Val Pro Glu Gly Ser Lys Pro Gly Thr Tyr Val Met Thr
                275                 280                 285

Val Thr Ala Ile Asp Ala Asp Pro Asn Ala Leu Asn Gly Met Leu
290                 295                 300

Arg Tyr Arg Ile Val Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                325                 330                 335

Leu Asp Arg Glu Lys Val Gln Gln Tyr Thr Leu Ile Ile Gln Ala Thr
                340                 345                 350

Asp Met Glu Gly Ile Pro Thr Tyr Gly Leu Ser Asn Thr Ala Thr Ala
                355                 360                 365

Val Ile Thr Val Thr Asp Val Asn Asp Asn Pro Pro Glu Phe Thr Ala
                370                 375                 380

Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
                405                 410                 415

Asn Ala Val Tyr Arg Ile Ser Gly Gly Asp Pro Thr Gly Arg Phe Ala
                420                 425                 430

Ile Gln Thr Asp Pro Asn Ser Asn Asp Gly Leu Val Thr Val Val Lys
                435                 440                 445

Pro Ile Asp Phe Glu Thr Asn Arg Met Phe Val Leu Thr Val Ala Ala
                450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                485                 490                 495

Phe Ala Pro Asn Pro Lys Ile Ile Arg Gln Glu Glu Gly Leu His Ala
                500                 505                 510

Gly Thr Met Leu Thr Thr Phe Thr Ala Gln Asp Pro Asp Arg Tyr Met
                515                 520                 525

Gln Gln Asn Ile Arg Tyr Thr Lys Leu Ser Asp Pro Ala Asn Trp Leu
530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
                565                 570                 575

Ala Ser Asp Asn Gly Ile Pro Pro Met Ser Gly Thr Gly Thr Leu Gln
                580                 585                 590

Ile Tyr Leu Leu Asp Ile Asn Asp Asn Ala Pro Gln Val Leu Pro Gln
                595                 600                 605

Glu Ala Glu Thr Cys Glu Thr Pro Asp Pro Asn Ser Ile Asn Ile Thr
                610                 615                 620

Ala Leu Asp Tyr Asp Ile Asp Pro Asn Ala Gly Pro Phe Ala Phe Asp
625                 630                 635                 640
```

-continued

```
Leu Pro Leu Ser Pro Val Thr Ile Lys Arg Asn Trp Thr Ile Thr Arg
                645                 650                 655
Leu Asn Gly Asp Phe Ala Gln Leu Asn Leu Lys Ile Lys Phe Leu Glu
            660                 665                 670
Ala Gly Ile Tyr Glu Val Pro Ile Ile Thr Asp Ser Gly Asn Pro
        675                 680                 685
Pro Lys Ser Asn Ile Ser Ile Leu Arg Val Lys Val Cys Gln Cys Asp
    690                 695                 700
Ser Asn Gly Asp Cys Thr Asp Val Asp Arg Ile Val Gly Ala Gly Leu
705                 710                 715                 720
Gly Thr Gly Ala Ile Ile Ala Ile Leu Leu Cys Ile Ile Leu Leu
                725                 730                 735
Ile Leu Val Leu Met Phe Val Val Trp Met Lys Arg Arg Asp Lys Glu
            740                 745                 750
Arg Gln Ala Lys Gln Leu Leu Ile Asp Pro Glu Asp Val Arg Asp
        755                 760                 765
Asn Ile Leu Lys Tyr Asp Glu Glu Gly Gly Gly Glu Glu Asp Gln Asp
    770                 775                 780
Tyr Asp Leu Ser Gln Leu Gln Gln Pro Asp Thr Val Glu Pro Asp Ala
785                 790                 795                 800
Ile Lys Pro Val Gly Ile Arg Arg Met Asp Glu Arg Pro Ile His Ala
                805                 810                 815
Glu Pro Gln Tyr Pro Val Arg Ser Ala Ala Pro His Pro Gly Asp Ile
            820                 825                 830
Gly Asp Phe Ile Asn Glu Gly Leu Lys Ala Ala Asp Asn Asp Pro Thr
        835                 840                 845
Ala Pro Pro Tyr Asp Ser Leu Leu Val Phe Asp Tyr Glu Gly Ser Gly
    850                 855                 860
Ser Thr Ala Gly Ser Leu Ser Ser Leu Asn Ser Ser Ser Ser Gly Gly
865                 870                 875                 880
Glu Gln Asp Tyr Asp Tyr Leu Asn Asp Trp Gly Pro Arg Phe Lys Lys
                885                 890                 895
Leu Ala Asp Met Tyr Gly Gly Gly Asp Asp
                900                 905
```

<210> SEQ ID NO 7
<211> LENGTH: 3170
<212> TYPE: DNA
<213> ORGANISM: Homo sapiens
<220> FEATURE:
<221> NAME/KEY: modified_base
<222> LOCATION: (2523)
<223> OTHER INFORMATION: a, c, t, g, unknown or other

<400> SEQUENCE: 7

```
ctccactcac gctcagccct ggacggacag gcagtccaac ggaacagaaa catccctcag      60
cccacaggca cgatctgttc ctcctgggaa gatgcagagg ctcatgatgc tcctcgccac     120
atcgggcgcc tgcctgggcc tgctggcagt ggcagcagtg gcagcagcag gtgctaaccc     180
tgcccaacgg gacacccaca gcctgctgcc cacccaccgg cgccaaaaga gagattggat     240
ttggaaccag atgcacattg atgaagagaa aaacacctca cttccccatc atgtaggcaa     300
gatcaagtca gcgtgagtc gcaagaatgc caagtacctg ctcaaaggag aatatgtggg     360
caagggtcttc cgggtcgatg cagagacagg agacgtgttc gccattgaga ggctggaccg     420
ggagaatatc tcagagtacc acctcactgc tgtcattgtg gacaaggaca ctggcgaaaa     480
```

```
cctggagact ccttccagct tcaccatcaa agttcatgac gtgaacgaca actggcctgt    540
gttcacgcat cggttgttca atgcgtccgt gcctgagtcg tcggctgtgg ggacctcagt    600
catctctgtg acagcagtgg atgcagacga ccccactgtg ggagaccacg cctctgtcat    660
gtaccaaatc ctgaagggga aagagtattt tgccatcgat aattctggac gtattatcac    720
aataacgaaa agcttggacc gagagaagca ggccaggtat gagatcgtgg tggaagcgcg    780
agatgcccag ggcctccggg gggactcggg cacggccacc gtgctggtca ctctgcaaga    840
catcaatgac aacttcccct tcttcaccca gaccaagtac acatttgtcg tgcctgaaga    900
cacccgtgtg ggcacctctg tgggctctct gtttgttgag acccagatg agccccagaa     960
ccggatgacc aagtacagca tcttgcgggg cgactaccag gacgctttca ccattgagac    1020
aaaccccgcc cacaacgagg gcatcatcaa gcccatgaag cctctggatt atgaatacat    1080
ccagcaatac agcttcatag tcgaggccac agacccacc atcgacctcc gatacatgag     1140
ccctcccgcg ggaaacagag cccaggtcat tatcaacatc acagatgtgg acgagccccc    1200
cattttccag cagcctttct accacttcca gctgaaggaa aaccagaaga agcctctgat    1260
tggcacagtg ctggccatgg accctgatgc ggctaggcat agcattggat actccatccg    1320
caggaccagt gacaagggcc agttcttccg agtcacaaaa aaggggggaca tttacaatga   1380
gaaagaactg gacagagaag tctacccctg gtataacctg actgtggagg ccaaagaact    1440
ggattccact ggaaccccca caggaaaaga atccattgtg caagtccaca ttgaagtttt    1500
ggatgagaat gacaatgccc cggagtttgc caagccctac cagcccaaag tgtgtgagaa    1560
cgctgtccat ggccagctgg tcctgcagat ctccgcaata gacaaggaca taacaccacg    1620
aaacgtgaag ttcaaattca tcttgaatac tgagaacaac tttaccctca cggataatca    1680
cgataacacg gccaacatca cagtcaagta tgggcagttt gaccgggagc ataccaaggt    1740
ccacttccta cccgtggtca tctcagacaa tgggatgcca agtcgcacgg gcaccagcac    1800
gctgaccgtg gccgtgtgca agtgcaacga gcagggcgag ttcacctcct gcgaggatat    1860
ggccgcccag gtgggcgtga gcatccaggc agtggtagcc atcttactct gcatcctcac    1920
catcacagtg atcaccctgc tcatcttcct gcggcggcgg ctccggaagc aggcccgcgc    1980
gcacggcaag agcgtgccgg agatccacga gcagctggtc acctacgacg aggagggcgg    2040
cggcgagatg gacaccacca gctacgatgt gtcggtgctc aactcggtgc cgcgcggcgg    2100
ggccaagccc cgcgcgccg cgctggacgc ccggccttcc ctctatgcgc aggtgcagaa    2160
gccaccgagg cacgcgcctg ggcacacgg agggcccggg gagatggcag ccatgatcga    2220
ggtgaagaag gacgaggcgg accacgacgg cgacggcccc ccctacgaca cgctgcacat    2280
ctacggctac gagggctccg agtccatagc cgagtccctc agctccctgg gcaccgactc    2340
atccgactct gacgtggatt acgacttcct taacgactgg ggacccaggt ttaagatgct    2400
ggctgagctg tacggctcgg accccgggga ggagctgctg tattaggcgg ccgaggtcac    2460
tctgggcctg gggaccccaaa cccctgcag cccaggccag tcagactcca ggcaccacag    2520
cvncadctcc aaaaatggca gtgactcccc agcccagcac cccttcctcg tgggtcccag    2580
agacctcatc agccttggga tagcaaactc caggttcctg aaatatccag gaatatatgt    2640
cagtgatgac tattctcaaa tgctggcaaa tccaggctgg tgttctgtct gggctcagac    2700
atccacataa ccctgtcacc cacagaccgc cgtctaactc aaagacttcc tctggctccc    2760
caaggctgca aagcaaaaca gactgtgttt aactgctgca gggtcttttt ctagggtccc    2820
```

-continued

```
tgaacgccct ggtaaggctg gtgaggtcct ggtgcctatc tgcctggagg caaaggcctg    2880
gacagcttga cttgtggggc aggattctct gcagcccatt cccaagggag actgaccatc    2940
atgccctctc tcgggagccc tagccctgct ccaactccat actccactcc aagtgcccca    3000
ccactcccca acccctctcc aggcctgtca agagggagga aggggcccca tggcagctcc    3060
tgaccttggg tcctgaagtg acctcactgg cctgccatgc cagtaactgt gctgtactga    3120
gcactgaacc acattcaggg aaatggctta ttaaactttg aagcaactgt                3170
```

<210> SEQ ID NO 8
<211> LENGTH: 780
<212> TYPE: PRT
<213> ORGANISM: Homo sapiens

<400> SEQUENCE: 8

```
Met Met Leu Leu Ala Thr Ser Gly Ala Cys Leu Gly Leu Leu Ala Val
1               5                   10                  15

Ala Ala Val Ala Ala Gly Ala Asn Pro Ala Gln Arg Asp Thr His
            20                  25                  30

Ser Leu Leu Pro Thr His Arg Arg Gln Lys Arg Asp Trp Ile Trp Asn
        35                  40                  45

Gln Met His Ile Asp Glu Glu Lys Asn Thr Ser Leu Pro His His Val
    50                  55                  60

Gly Lys Ile Lys Ser Ser Val Ser Arg Lys Asn Ala Lys Tyr Leu Leu
65                  70                  75                  80

Lys Gly Glu Tyr Val Gly Lys Val Phe Arg Val Asp Ala Glu Thr Gly
                85                  90                  95

Asp Val Phe Ala Ile Glu Arg Leu Asp Arg Glu Asn Ile Ser Glu Tyr
            100                 105                 110

His Leu Thr Ala Val Ile Val Asp Lys Asp Thr Gly Glu Asn Leu Glu
        115                 120                 125

Thr Pro Ser Ser Phe Thr Ile Lys Val His Asp Val Asn Asp Asn Trp
    130                 135                 140

Pro Val Phe Thr His Arg Leu Phe Asn Ala Ser Val Pro Glu Ser Ser
145                 150                 155                 160

Ala Val Gly Thr Ser Val Ile Ser Val Thr Ala Val Asp Ala Asp Asp
                165                 170                 175

Pro Thr Val Gly Asp His Ala Ser Val Met Tyr Gln Ile Leu Lys Gly
            180                 185                 190

Lys Glu Tyr Phe Ala Ile Asp Asn Ser Gly Arg Ile Ile Thr Ile Thr
        195                 200                 205

Lys Ser Leu Asp Arg Glu Lys Gln Ala Arg Tyr Glu Ile Val Val Glu
    210                 215                 220

Ala Arg Asp Ala Gln Gly Leu Arg Gly Asp Ser Gly Thr Ala Thr Val
225                 230                 235                 240

Leu Val Thr Leu Gln Asp Ile Asn Asp Asn Phe Pro Phe Phe Thr Gln
                245                 250                 255

Thr Lys Tyr Thr Phe Val Val Pro Glu Asp Thr Arg Val Gly Thr Ser
            260                 265                 270

Val Gly Ser Leu Phe Val Glu Asp Pro Asp Glu Pro Gln Asn Arg Met
        275                 280                 285

Thr Lys Tyr Ser Ile Leu Arg Gly Asp Tyr Gln Asp Ala Phe Thr Ile
    290                 295                 300

Glu Thr Asn Pro Ala His Asn Glu Gly Ile Ile Lys Pro Met Lys Pro
305                 310                 315                 320
```

-continued

Leu Asp Tyr Glu Tyr Ile Gln Gln Tyr Ser Phe Ile Val Glu Ala Thr
            325                 330                 335

Asp Pro Thr Ile Asp Leu Arg Tyr Met Ser Pro Ala Gly Asn Arg
            340                 345             350

Ala Gln Val Ile Ile Asn Ile Thr Asp Val Asp Glu Pro Pro Ile Phe
            355                 360                 365

Gln Gln Pro Phe Tyr His Phe Gln Leu Lys Glu Asn Gln Lys Lys Pro
    370                 375                 380

Leu Ile Gly Thr Val Leu Ala Met Asp Pro Asp Ala Ala Arg His Ser
385                 390                 395                 400

Ile Gly Tyr Ser Ile Arg Arg Thr Ser Asp Lys Gly Gln Phe Phe Arg
                405                 410                 415

Val Thr Lys Lys Gly Asp Ile Tyr Asn Glu Lys Glu Leu Asp Arg Glu
            420                 425                 430

Val Tyr Pro Trp Tyr Asn Leu Thr Val Glu Ala Lys Glu Leu Asp Ser
            435                 440                 445

Thr Gly Thr Pro Thr Gly Lys Glu Ser Ile Val Gln Val His Ile Glu
    450                 455                 460

Val Leu Asp Glu Asn Asp Asn Ala Pro Glu Phe Ala Lys Pro Tyr Gln
465                 470                 475                 480

Pro Lys Val Cys Glu Asn Ala Val His Gly Gln Leu Val Leu Gln Ile
            485                 490                 495

Ser Ala Ile Asp Lys Asp Ile Thr Pro Arg Asn Val Lys Phe Lys Phe
                500                 505                 510

Ile Leu Asn Thr Glu Asn Asn Phe Thr Leu Thr Asp Asn His Asp Asn
            515                 520                 525

Thr Ala Asn Ile Thr Val Lys Tyr Gly Gln Phe Asp Arg Glu His Thr
            530                 535                 540

Lys Val His Phe Leu Pro Val Val Ile Ser Asp Asn Gly Met Pro Ser
545                 550                 555                 560

Arg Thr Gly Thr Ser Thr Leu Thr Val Ala Val Cys Lys Cys Asn Glu
                565                 570                 575

Gln Gly Glu Phe Thr Phe Cys Glu Asp Met Ala Ala Gln Val Gly Val
            580                 585                 590

Ser Ile Gln Ala Val Val Ala Ile Leu Leu Cys Ile Leu Thr Ile Thr
            595                 600                 605

Val Ile Thr Leu Leu Ile Phe Leu Arg Arg Arg Leu Arg Lys Gln Ala
        610                 615                 620

Arg Ala His Gly Lys Ser Val Pro Glu Ile His Glu Gln Leu Val Thr
625                 630                 635                 640

Tyr Asp Glu Glu Gly Gly Gly Glu Met Asp Thr Thr Ser Tyr Asp Val
                645                 650                 655

Ser Val Leu Asn Ser Val Arg Arg Gly Gly Ala Lys Pro Pro Arg Pro
            660                 665                 670

Ala Leu Asp Ala Arg Pro Ser Leu Tyr Ala Gln Val Gln Lys Pro Pro
            675                 680                 685

Arg His Ala Pro Gly Ala His Gly Gly Pro Gly Glu Met Ala Ala Met
    690                 695                 700

Ile Glu Val Lys Lys Asp Glu Ala Asp His Asp Gly Asp Gly Pro Pro
705                 710                 715                 720

Tyr Asp Thr Leu His Ile Tyr Gly Tyr Glu Gly Ser Glu Ser Ile Ala
                725                 730                 735

```
Glu Ser Leu Ser Ser Leu Gly Thr Asp Ser Ser Asp Ser Asp Val Asp
            740                 745                 750

Tyr Asp Phe Leu Asn Asp Trp Gly Pro Arg Phe Lys Met Leu Ala Glu
            755                 760                 765

Leu Tyr Gly Ser Asp Pro Arg Glu Glu Leu Leu Tyr
        770                 775             780

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaatccattg tgcaagtcca c                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acccctggta taacctgact                                                20
```